United States Patent
Yoo et al.

(10) Patent No.: US 10,247,867 B2
(45) Date of Patent: Apr. 2, 2019

(54) MONOMER, POLYMER, COMPENSATION FILM, OPTICAL FILM, AND DISPLAY DEVICE

(71) Applicant: SAMSUNG ELECTRONICS CO., LTD., Suwon-si, Gyeonggi-do (KR)

(72) Inventors: Joungeun Yoo, Seongnam-si (KR); Dmitry Androsov, Suwon-si (KR); Changki Kim, Suwon-si (KR); Kitae Park, Suwon-si (KR)

(73) Assignee: SAMSUNG ELECTRONICS CO., LTD., Gyeonggi-Do (KR)

( * ) Notice: Subject to any disclaimer, the term of this patent is extended or adjusted under 35 U.S.C. 154(b) by 276 days.

(21) Appl. No.: 15/242,862

(22) Filed: Aug. 22, 2016

(65) Prior Publication Data

US 2017/0059755 A1    Mar. 2, 2017

(30) Foreign Application Priority Data

Aug. 28, 2015   (KR) .................. 10-2015-0121502

(51) Int. Cl.
| | |
|---|---|
| *C08G 73/10* | (2006.01) |
| *G02B 5/30* | (2006.01) |
| *C07C 211/51* | (2006.01) |
| *C07C 229/60* | (2006.01) |
| *C08J 5/18* | (2006.01) |

(52) U.S. Cl.
CPC ............ *G02B 5/305* (2013.01); *C07C 211/51* (2013.01); *C07C 229/60* (2013.01); *C08G 73/10* (2013.01); *C08G 73/1007* (2013.01); *C08G 73/1039* (2013.01); *C08G 73/1042* (2013.01); *C08G 73/1046* (2013.01); *C08G 73/1053* (2013.01); *C08G 73/1082* (2013.01); *C08J 5/18* (2013.01); *C08J 2379/08* (2013.01)

(58) Field of Classification Search
CPC ...... C08G 73/1067; C08G 73/12; C08L 79/08
See application file for complete search history.

(56) References Cited

U.S. PATENT DOCUMENTS

| | | | | |
|---|---|---|---|---|
| 4,038,320 A | * | 7/1977 | Arnold .................. | C07C 205/06 526/285 |
| 4,365,093 A | * | 12/1982 | Diamond ............. | A61K 31/135 564/305 |
| 5,689,004 A | * | 11/1997 | Connell ................ | C07C 217/90 564/328 |
| 7,811,467 B2 | | 10/2010 | Yamahara et al. | |
| 2007/0232780 A1 | | 10/2007 | Tamura | |
| 2010/0003490 A1 | | 1/2010 | Lida et al. | |

FOREIGN PATENT DOCUMENTS

| | | |
|---|---|---|
| JP | 2001-056469 A | 2/2001 |
| JP | 2001-089427 A | 4/2001 |
| KR | 2012-0079810 A | 7/2012 |

OTHER PUBLICATIONS

Mark W. Beltz et al., "Synthesis and properties of aromatic polyimides containing oxyalkylene linkages", High Perform. Polym. 7 (1995) 23-40.
Extended European Search Report dated Feb. 6, 2017, issued for the corresponding European Patent Application No. 16184785.0.

* cited by examiner

*Primary Examiner* — Gregory Listvoyb
(74) *Attorney, Agent, or Firm* — Cantor Colburn LLP

(57) ABSTRACT

A monomer represented by Chemical Formula 1-1

Chemical Formula 1-1

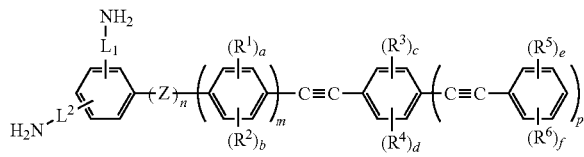

wherein in Chemical Formula 1-1, Z, $L^1$, $L^2$, $R^1$ to $R^6$, n, m, p, and a to f are the same as defined in the detailed description.

8 Claims, 3 Drawing Sheets

MONOMER, POLYMER, COMPENSATION FILM, OPTICAL FILM, AND DISPLAY DEVICE

CROSS-REFERENCE TO RELATED APPLICATIONS

This application claims priority to Korean Patent Application No. 10-2015-0121502 filed in the Korean Intellectual Property Office on Aug. 28, 2015, and all the benefits accruing therefrom under 35 U.S.C. § 119, the content of which is incorporated herein in its entirety by reference.

BACKGROUND

1. Field

A monomer, a polymer, a compensation film, an optical film, and a display device are disclosed.

2. Description of the Related Art

A flat panel displays may be classified into a light-emitting display device emitting light by itself and a non-emissive display device requiring a separate light source, and a compensation film or an optical film is frequently employed for improving the image quality thereof. There still remains a need in novel polymers, which can improve the properties of the existing compensation and optical films.

SUMMARY

An embodiment provides a novel monomer that is applicable to a compensation film.

Another embodiment provides a polymer including a moiety derived from the novel monomer by polymerization of the novel monomer.

Yet another embodiment provides a compensation film including the polymer.

Still another embodiment provides an optical film including the compensation film.

A further embodiment provides a display device including the compensation film or the optical film.

According to an embodiment, a monomer represented by Chemical Formula 1-1 is provided.

Chemical Formula 1-1

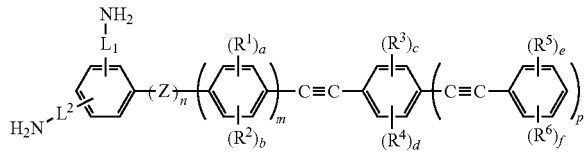

In Chemical Formula 1-1,

Z is —O—, —C=O—, —(C=O)O—, —O(C=O)—, —CH$_2$O—, —CF$_2$O—, —OC(=O)O—, —C≡C—, —CH=CH—, —CF=CF—, or —C(=O)NR$^a$—,

L$^1$ and L$^2$ are independently a single bond, a substituted or unsubstituted C1 to C20 alkylene group, a substituted or unsubstituted C1 to C20 oxyalkylene group, a substituted or unsubstituted C3 to C20 cycloalkylene group, a substituted or unsubstituted C3 to C20 oxycycloalkylene group, a substituted or unsubstituted C6 to C20 arylene group, a substituted or unsubstituted C6 to C20 oxyarylene group, a substituted or unsubstituted C3 to C20 divalent heterocyclic group, or a combination thereof, R$^1$ to R$^6$ and R$^a$ are independently hydrogen, a substituted or unsubstituted C1 to C20 alkyl group, a substituted or unsubstituted C1 to C20 alkoxy group, a substituted or unsubstituted C2 to C20 alkoxyalkyl group, a substituted or unsubstituted C1 to C20 fluoroalkyl group, a substituted or unsubstituted C3 to C20 cycloalkyl group, a substituted or unsubstituted C3 to C20 cycloalkyloxy group, a substituted or unsubstituted C4 to C20 cycloalkoxyalkyl group, a substituted or unsubstituted C6 to C20 aryl group, a substituted or unsubstituted C6 to C20 aryloxy group, a substituted or unsubstituted C7 to C20 arylalkyl group, a substituted or unsubstituted C7 to C20 aryloxyalkyl group, a substituted or unsubstituted C3 to C20 heterocyclic group, a substituted or unsubstituted silyl group, a hydroxy group, a halogen, a nitro group, or a combination thereof, n and m are independently 0 or 1, p is an integer ranging from 1 to 3, a to f are independently integers ranging from 0 to 4, and a+b, c+d, and e+f are independently integers of less than or equal to 4. The monomer may be represented by Chemical Formula 1-1a or 1-1b.

Chemical Formula 1-1a

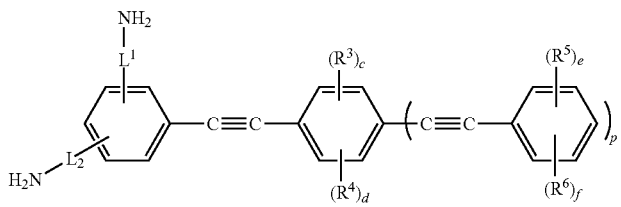

Chemical Formula 1-1b

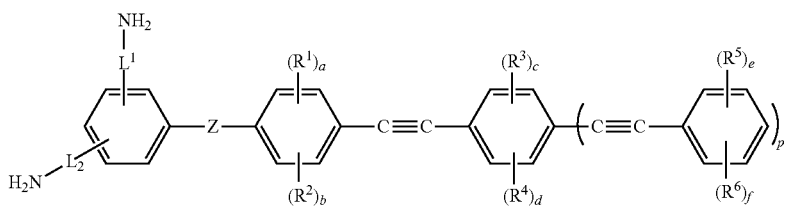

In Chemical Formulae 1-1a and 1-1b,

Z is —C=O—, —(C=O)O—, —O(C=O)—, —CH$_2$O—, —CF$_2$O—, —OC(=O)O—, —C≡C—, —CH=CH—, —CF=CF—, or —C(=O)NR$^a$—,

L$^1$ and L$^2$ are independently a single bond, a substituted or unsubstituted C1 to C20 alkylene group, a substituted or unsubstituted C1 to C20 oxyalkylene group, a substituted or unsubstituted C3 to C20 cycloalkylene group, a substituted or unsubstituted C3 to C20 oxycycloalkylene group, a substituted or unsubstituted C6 to C20 arylene group, a substituted or unsubstituted C6 to C20 oxyarylene group, a substituted or unsubstituted C3 to C20 divalent heterocyclic group, or a combination thereof, R$^1$ to R$^6$ and R$^a$ are independently hydrogen, a substituted or unsubstituted C1 to C20 alkyl group, a substituted or unsubstituted C1 to C20 alkoxy group, a substituted or unsubstituted C2 to C20 alkoxyalkyl group, a substituted or unsubstituted C1 to C20 fluoroalkyl group, a substituted or unsubstituted C3 to C20 cycloalkyl group, a substituted or unsubstituted C3 to C20 cycloalkyloxy group, a substituted or unsubstituted C4 to C20 cycloalkoxyalkyl group, a substituted or unsubstituted C6 to C20 aryl group, a substituted or unsubstituted C6 to C20 aryloxy group, a substituted or unsubstituted C7 to C20 arylalkyl group, a substituted or unsubstituted C7 to C20 aryloxyalkyl group, a substituted or unsubstituted C3 to C20 heterocyclic group, a substituted or unsubstituted silyl group, a hydroxy group, a halogen, a nitro group, or a combination thereof, p is an integer ranging from 1 to 3, a to f are independently integers ranging from 0 to 4, and a+b, c+d, and e+f are independently integers of less than or equal to 4.

The monomer may be represented by Chemical Formula 1a or 1b.

Chemical Formula 1a

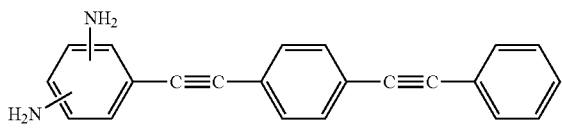

Chemical Formula 1b

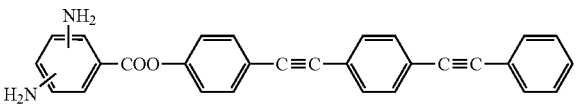

According to another embodiment, a polymer, which is a reaction product of an anhydride and a diamine compound, wherein the diamine compound includes a first diamine compound represented by Chemical Formula 1-1, is provided.

The first diamine compound may be represented by Chemical Formula 1-1a or 1-1b.

The first diamine compound may be represented by Chemical Formula 1a or 1b.

The diamine compound may further include a second diamine compound, which is different from the first diamine compound, wherein the second diamine compound may include at least one selected from compounds of Group 1.

Group 1

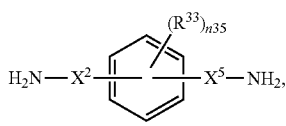

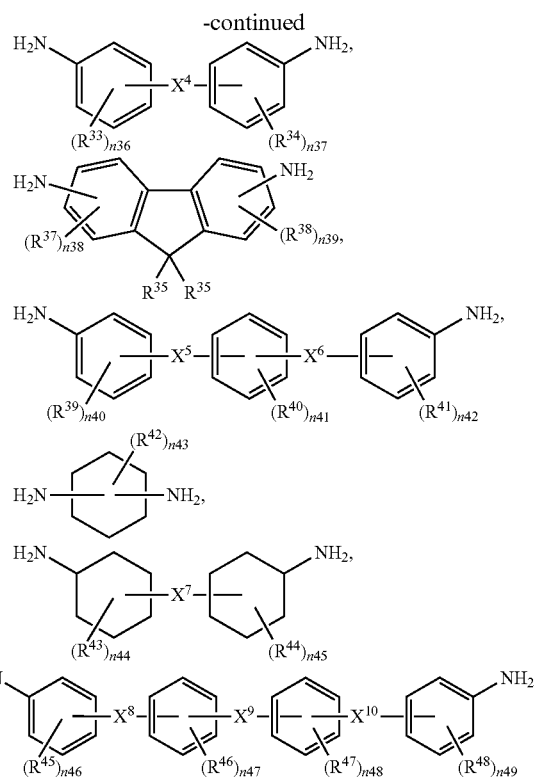

In Group 1,

R$^{32}$ to R$^{48}$ are independently hydrogen, a substituted or unsubstituted C1 to C20 alkyl group, a substituted or unsubstituted C1 to C20 alkoxy group, a substituted or unsubstituted C1 to C20 fluoroalkyl group, a substituted or unsubstituted C3 to C20 cycloalkyl group, a substituted or unsubstituted C3 to C20 heterocyclic group, a substituted or unsubstituted C3 to C20 cycloalkoxy group, a substituted or unsubstituted C6 to C20 aryl group, a substituted or unsubstituted C6 to C20 aryloxy group, a substituted or unsubstituted amine group, a substituted or unsubstituted C1 to C20 alkylamine group, a substituted or unsubstituted silyl group, a hydroxy group, a halogen, a nitro group, or a combination thereof, X$^2$ to X$^{10}$ are independently a single bond, a substituted or unsubstituted C1 to C20 alkylene group, a substituted or unsubstituted C3 to C20 cycloalkylene group, a substituted or unsubstituted C6 to C20 arylene group, a substituted or unsubstituted C3 to C20 divalent heterocyclic group, —SO$_2$—, —O—, —C(=O)—, —C(=O)O—, a group selected from Group 2, or a combination thereof, n35 to n37 and n40 to n49 are independently an integer ranging from 0 to 4, and n38 and n39 are independently an integer ranging from 0 to 3.

Group 2

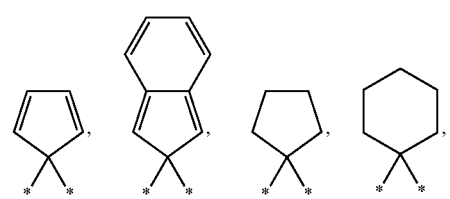

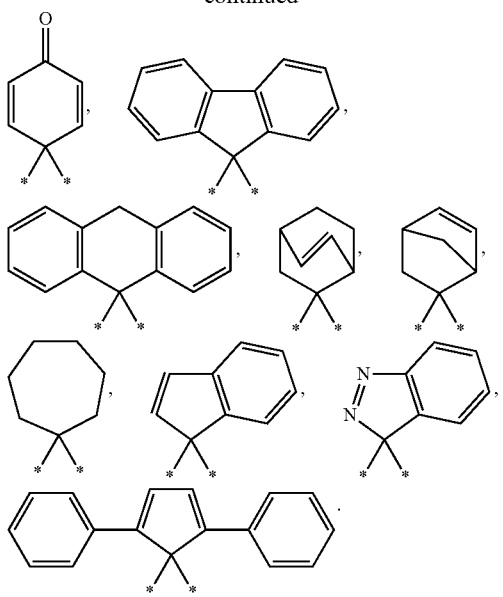
The second diamine compound may include at least one selected from compounds of Group 3.
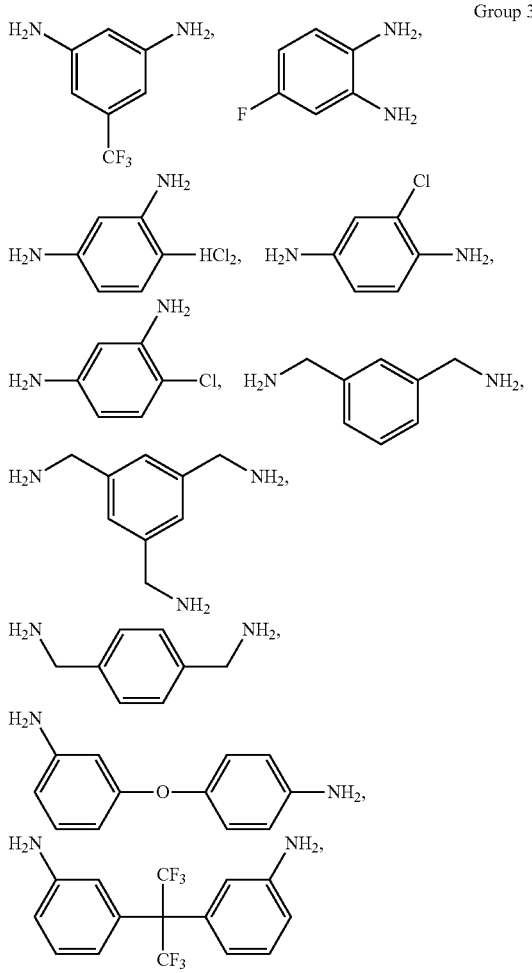
Group 3
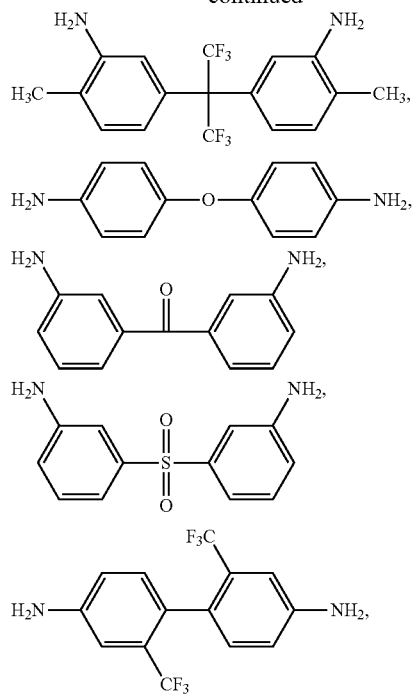

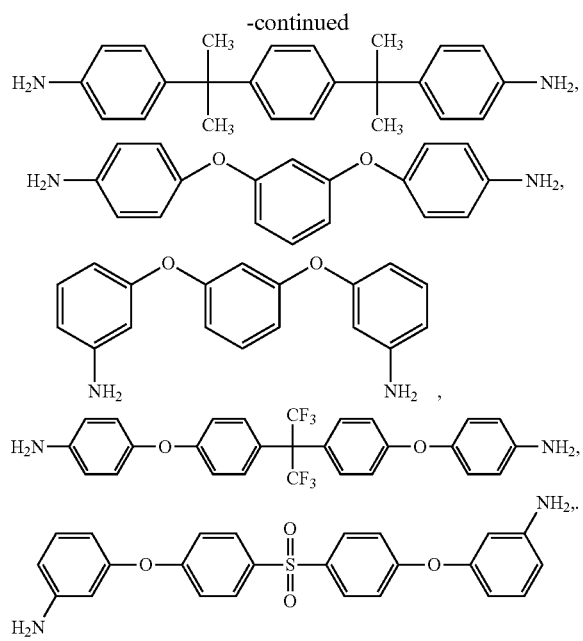

A mole ratio of the first diamine compound and the second diamine compound may be about 1:9 to about 5:5.

The anhydride may be represented by Chemical Formula 2 or 3.

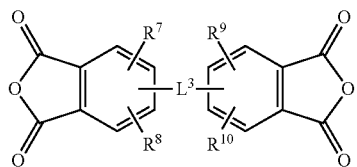

Chemical Formula 2

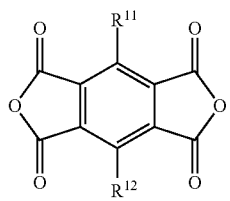

Chemical Formula 3

In Chemical Formula 2 or 3, $L^3$ is a single bond, a substituted or unsubstituted C1 to C20 alkylene group, a substituted or unsubstituted C1 to C20 oxyalkylene group, a substituted or unsubstituted C3 to C20 cycloalkylene group, a substituted or unsubstituted C3 to C20 oxycycloalkylene group, a substituted or unsubstituted C6 to C20 arylene group, a substituted or unsubstituted C6 to C20 oxyarylene group, a substituted or unsubstituted C3 to C20 divalent heterocyclic group, —O—, —C(=O)—, —C(=O)O—, —SO$_2$—, or —C(=O)NR$^b$—, or a combination thereof, and $R^7$ to $R^{12}$ and $R^b$ are independently hydrogen, a substituted or unsubstituted C1 to C20 alkyl group, a substituted or unsubstituted C1 to C20 alkoxy group, a substituted or unsubstituted C2 to C20 alkoxyalkyl group, a substituted or unsubstituted C1 to C20 fluoroalkyl group, a substituted or unsubstituted C3 to C20 cycloalkyl group, a substituted or unsubstituted C3 to C20 cycloalkyloxy group, a substituted or unsubstituted C4 to C20 cycloalkoxyalkyl group, a substituted or unsubstituted C6 to C20 aryl group, a substituted or unsubstituted C6 to C20 aryloxy group, a substituted or unsubstituted C7 to C20 arylalkyl group, a substituted or unsubstituted C7 to C20 aryloxyalkyl group, a substituted or unsubstituted C3 to C20 heterocyclic group, a substituted or unsubstituted silyl group, a hydroxy group, a halogen, a nitro group, or a combination thereof.

The anhydride may include 2,3,3',4'-biphenyltetracarboxylic dianhydride, 2,3,3',4'-diphenylsulfone tetracarboxylic dianhydride, 3,4'-oxydiphthalic anhydride, 3,3',4,4'-biphenyl tetracarboxylic dianhydride, bicyclo[2.2.2]oct-7-ene-2,3,5,6-tetracarboxylic dianhydride, 3,3',4,4'-diphenylsulfone tetracarboxylic dianhydride, 4,4'-(hexafluoroisopropylidene)diphthalic anhydride, 4,4'-oxydiphthalic anhydride, pyromellitic dianhydride, 4-(2,5-dioxotetrahydrofuran-3-yl)-1,2,3,4-tetrahydronaphthalene-1,2-dicarboxylic anhydride, or a combination thereof.

According to another embodiment, a compensation film includes a polymer, which is a reaction product of an anhydride and a diamine compound, wherein the polymer includes a side chain including at least one acetylene group.

The diamine compound may include a first diamine compound represented by Chemical Formula 1-2.

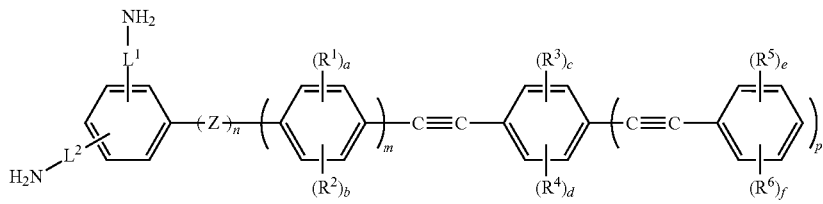

Chemical Formula 1-2

In Chemical Formula 1-2,

Z is —C=O—, —(C=O)O—, —O(C=O)—, —CH$_2$O—, —CF$_2$O—, —OC(=O)O—, —C≡C—, —CH=CH—, —CF=CF—, or —C(=O)NR$^a$—, $L^1$ and $L^2$ are independently a single bond, a substituted or unsubstituted C1 to C20 alkylene group, a substituted or unsubstituted C1 to C20 oxyalkylene group, a substituted or unsubstituted C3 to C20 cycloalkylene group, a substituted or unsubstituted C3 to C20 oxycycloalkylene group, a substituted or unsubstituted C6 to C20 arylene group, a substituted or unsubstituted C6 to C20 oxyarylene group, a substituted or unsubstituted C3 to C20 divalent heterocyclic group, or a combination thereof, $R^1$ to $R^6$ and $R^a$ are independently hydrogen, a substituted or unsubstituted C1 to C20 alkyl group, a substituted or unsubstituted C1 to C20 alkoxy group, a substituted or unsubstituted C2 to C20 alkoxyalkyl group, a substituted or unsubstituted C1 to C20 fluoroalkyl group, a substituted or unsubstituted C3 to C20 cycloalkyl group, a substituted or unsubstituted C3 to C20 cycloalkyloxy group, a substituted or unsubstituted C4 to C20 cycloalkoxyalkyl group, a substituted or unsubstituted C6 to C20 aryl group, a substituted or unsubstituted C6 to C20 aryloxy group, a substituted or unsubstituted C7 to C20 arylalkyl group, a substituted or unsubstituted C7 to C20 aryloxyalkyl group, a substituted or unsubstituted C3 to C20 heterocyclic group, a substituted or unsubstituted silyl group, a hydroxy group, a halogen, a nitro group, or a combination thereof, n and m are independently 0 or 1, p is an integer ranging from 0 to 3, for example p is an integer ranging from 1 to 3, a to f are independently integers ranging from 0 to 4, and a+b, c+d, and e+f are independently integers of less than or equal to 4.

The first diamine compound may be represented by Chemical Formula 1-2a or 1-2b.

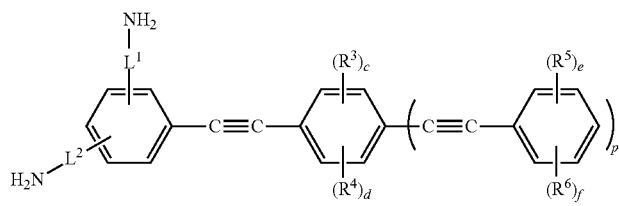

Chemical Formula 1-2a

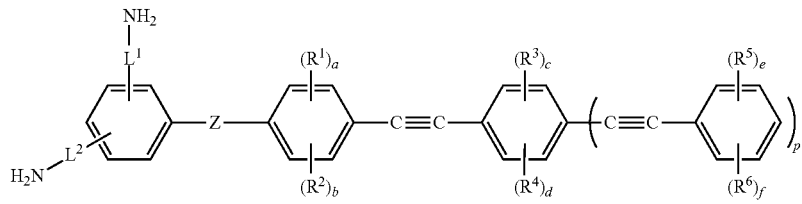

Chemical Formula 1-2b

In Chemical Formulae 1-2a and 1-2b,

Z is —C═O—, —(C═O)O—, —O(C═O)—, —CH$_2$O—, —CF$_2$O—, —OC(═O)O—, —C≡C—, —CH═CH—, —CF═CF—, or —C(═O)NR$^a$—,

L$^1$ and L$^2$ are independently a single bond, a substituted or unsubstituted C1 to C20 alkylene group, a substituted or unsubstituted C1 to C20 oxyalkylene group, a substituted or unsubstituted C3 to C20 cycloalkylene group, a substituted or unsubstituted C3 to C20 oxycycloalkylene group, a substituted or unsubstituted C6 to C20 arylene group, a substituted or unsubstituted C6 to C20 oxyarylene group, a substituted or unsubstituted C3 to C20 divalent heterocyclic group, or a combination thereof, R$^1$ to R$^6$ and R$^a$ are independently hydrogen, a substituted or unsubstituted C1 to C20 alkyl group, a substituted or unsubstituted C1 to C20 alkoxy group, a substituted or unsubstituted C2 to C20 alkoxyalkyl group, a substituted or unsubstituted C1 to C20 fluoroalkyl group, a substituted or unsubstituted C3 to C20 cycloalkyl group, a substituted or unsubstituted C3 to C20 cycloalkyloxy group, a substituted or unsubstituted C4 to C20 cycloalkoxyalkyl group, a substituted or unsubstituted C6 to C20 aryl group, a substituted or unsubstituted C6 to C20 aryloxy group, a substituted or unsubstituted C7 to C20 arylalkyl group, a substituted or unsubstituted C7 to C20 aryloxyalkyl group, a substituted or unsubstituted C3 to C20 heterocyclic group, a substituted or unsubstituted silyl group, a hydroxy group, a halogen, a nitro group, or a combination thereof, and p is an integer ranging from 0 to 3, for example p is an integer ranging from 1 to 3, a to f are independently integers ranging from 0 to 4, and a+b, c+d, and e+f are independently integers of less than or equal to 4.

The first diamine compound may be represented by one of Chemical Formulae 1a to 1d.

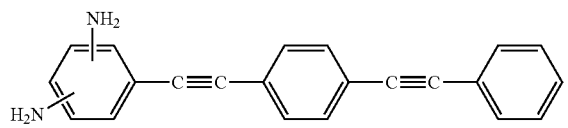

Chemical Formula 1a

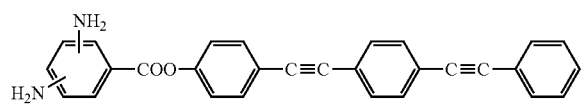

Chemical Formula 1b

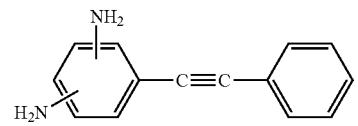

Chemical Formula 1c

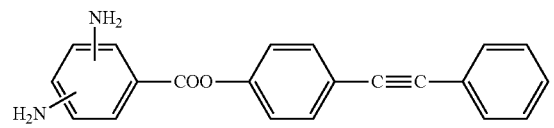

Chemical Formula 1d

The diamine compound may include a second diamine compound, which is different from the first diamine compound, wherein the second diamine compound may include at least one selected from compounds of Group 1.

The second diamine compound may include at least one selected from Group 3.

A mole ratio of the first diamine compound and the second diamine compound may be about 1:9 to about 5:5.

The anhydride may be represented by Chemical Formula 2 or 3.

The anhydride may include 2,3,3',4'-biphenyltetracarboxylic dianhydride, 2,3,3',4'-diphenylsulfone tetracarboxylic dianhydride, 3,4'-oxydiphthalic anhydride, 3,3',4,4'-biphenyl tetracarboxylic dianhydride, bicyclo[2.2.2]oct-7-ene-2,3,5,6-tetracarboxylic dianhydride, 3,3',4,4'-diphenylsulfone tetracarboxylic dianhydride, 4,4'-(hexafluoroisopropylidene)diphthalic anhydride, 4,4'-oxydiphthalic anhydride, pyromellitic dianhydride, 4-(2,5-dioxotetrahydrofuran-3-yl)-1,2,3,4-tetrahydronaphthalene-1,2-dicarboxylic anhydride, or a combination thereof.

The compensation film may be elongated in a uniaxial direction.

Retardation of the compensation film at a 550 nanometer wavelength may be about 110 nanometers to about 160 nanometers.

Retardation values (R) of the compensation film at a 450 nanometer wavelength, a 550 nanometer wavelength, and a 650 nanometer wavelength may satisfy one of Relationship Equations 1 to 5.

$$R(450 \text{ nanometers}) \leq R(550 \text{ nanometers}) < R(650 \text{ nanometers}) \quad \text{Relationship Equation 1}$$

$$R(450 \text{ nanometers}) < R(550 \text{ nanometers}) \leq R(650 \text{ nanometers}) \quad \text{Relationship Equation 2}$$

$$R(450 \text{ nanometers}) \geq R(550 \text{ nanometers}) > R(650 \text{ nanometers}) \quad \text{Relationship Equation 3}$$

$$R(450 \text{ nanometers}) > R(550 \text{ nanometers}) \geq R(650 \text{ nanometers}) \quad \text{Relationship Equation 4}$$

$$R(450 \text{ nanometers}) = R(550 \text{ nanometers}) = R(650 \text{ nanometers}) \quad \text{Relationship Equation 5}$$

According to another embodiment, an optical film includes the compensation film and a polarization film.

The polarization film may be made of a melt-blend of a hydrophobic polymer and a dichroic dye.

According to yet another embodiment, a display device includes the compensation film or the optical film.

BRIEF DESCRIPTION OF THE DRAWINGS

The above and other aspects, advantages and features of this disclosure will become more apparent by describing in further detail exemplary embodiments thereof with reference to the accompanying drawings, in which.

DETAILED DESCRIPTION

Figure 1:
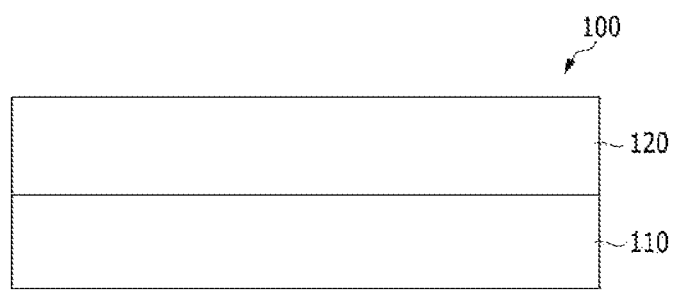
FIG. 1 is a schematic cross-sectional view showing an optical film according to an embodiment.

Exemplary embodiments of the present disclosure will hereinafter be described in detail, and may be easily performed by those who have common knowledge in the related art. However, this disclosure may be embodied in many different forms, and is not construed as limited to the exemplary embodiments set forth herein.

In the drawings, the thickness of layers, films, panels, regions, etc., are exaggerated for clarity. Like reference numerals designate like elements throughout the specification. It will be understood that when an element such as a layer, film, region, or substrate is referred to as being "on" another element, it can be directly on the other element or intervening elements may also be present. In contrast, when an element is referred to as being "directly on" another element, there are no intervening elements present.

Accordingly, the embodiments are merely described below, by referring to the figures, to explain aspects of the present description. As used herein, the term "and/or" includes any and all combinations of one or more of the associated listed items. The term "or" means "and/or." Expressions such as "at least one of" when preceding a list of elements, modify the entire list of elements and do not modify the individual elements of the list.

It will be understood that when an element is referred to as being "on" another element, it may be directly on the other element or intervening elements may be present therebetween. In contrast, when an element is referred to as being "directly on" another element, there are no intervening elements present.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another element, component, region, layer, or section. Thus, a first element, component, region, layer, or section discussed below could be termed a second element, component, region, layer, or section without departing from the teachings of the present embodiments.

The terminology used herein is for the purpose of describing particular embodiments only and is not intended to be limiting. As used herein, the singular forms "a," "an" and "the" are intended to include the plural forms as well, unless the context clearly indicates otherwise. The term "or" means "and/or." As used herein, the term "and/or" includes any and all combinations of one or more of the associated listed items. Expressions such as "at least one of," when preceding a list of elements, modify the entire list of elements and do not modify the individual elements of the list.

It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

"About" or "approximately" as used herein is inclusive of the stated value and means within an acceptable range of deviation for the particular value as determined by one of ordinary skill in the art, considering the measurement in question and the error associated with measurement of the particular quantity (i.e., the limitations of the measurement system).

Unless otherwise defined, all terms (including technical and scientific terms) used herein have the same meaning as commonly understood by one of ordinary skill in the art to which this general inventive concept belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments are described herein with reference to cross section illustrations that are schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims.

"Mixture" as used herein is inclusive of all types of combinations, including blends, alloys, solutions, and the like.

As used herein, when specific definition is not otherwise provided, the term "substituted" refers to one substituted with a substituent selected from a halogen (F, Br, Cl, or I), a hydroxy group, an alkoxy group, a nitro group, a cyano group, an amino group, an azido group, an amidino group, a hydrazino group, a hydrazono group, a carbonyl group, a carbamoyl group, a thiol group, an ester group, a carboxyl group or a salt thereof, a sulfonic acid group or a salt thereof, phosphoric acid or a salt thereof, a C1 to C20 alkyl group, a C2 to C20 alkenyl group, a C2 to C20 alkynyl group, a C6 to C30 aryl group, a C7 to C30 arylalkyl group, a C1 to C30 alkoxy group, a C1 to C20 heteroalkyl group, a C3 to C20 heteroarylalkyl group, a C3 to C30 cycloalkyl group, a C3 to C15 cycloalkenyl group, a C6 to C15 cycloalkynyl group, a C3 to C30 heterocycloalkyl group, and a combination thereof, instead of hydrogen of a compound or a group.

When a group containing a specified number of carbon atoms is substituted with any of the groups listed in the preceding paragraph, the number of carbon atoms in the resulting "substituted" group is defined as the sum of the carbon atoms contained in the original (unsubstituted) group and the carbon atoms (if any) contained in the substituent. For example, when the term "substituted C1 to C20 alkyl" refers to a C1 to C20 alkyl group substituted with a C6 to C20 aryl group, the total number of carbon atoms in the resulting aryl substituted alkyl group is C7 to C40.

As used herein, when a definition is not otherwise provided, the term "alkyl" indicates a group derived from a completely saturated, branched or unbranched (or a straight or linear) hydrocarbon and having a specified number of carbon atoms.

As used herein, when a definition is not otherwise provided, the term "alkoxy" represents "alkyl-O—", wherein the term "alkyl" has the same meaning as described above.

As used herein, when a definition is not otherwise provided, the term "alkoxyalkyl" indicates an alkyl group substituted with one or more alkoxy groups, wherein the terms "alkyl" and "alkoxy" have the same meaning as described above.

As used herein, when a definition is not otherwise provided, the term "fluoroalkyl" indicates an alkyl group substituted with one or more fluorine groups, wherein the term "alkyl" has the same meaning as described above.

As used herein, when a definition is not otherwise provided, the term "cycloalkyl" indicates a monovalent group having one or more saturated rings in which all ring members are carbon.

As used herein, when a definition is not otherwise provided, the term "cycloalkyloxy" represents "cycloalkyl-O—", wherein the term "cycloalkyl" has the same meaning as described above.

As used herein, when a definition is not otherwise provided, the term "cycloalkoxyalkyl" indicates an alkyl group substituted with one or more cycloalkoxy groups, wherein the terms "alkyl" and "cycloalkoxy" have the same meaning as described above.

As used herein, when a definition is not otherwise provided, the term "aryl" indicates a group derived from an aromatic hydrocarbon containing at least one ring and having the specified number of carbon atoms.

As used herein, when a definition is not otherwise provided, the term "silyl" indicates "$R_3Si—$", wherein each R is independently "hydrogen", "alkyl" or "aryl" having the same meaning as described above.

As used herein, the term "alkylene" indicates a straight or branched saturated aliphatic hydrocarbon group having a valence of at least two, optionally substituted with one or more substituents where indicated, provided that the valence of the alkylene group is not exceeded.

As used herein, when a definition is not otherwise provided, the term "oxyalkylene" indicates an alkylene group in which any one or more methylene groups (—$CH_2$—) is substituted with an oxygen group (—O—), wherein the term "alkylene" has the same meaning as described above.

As used herein, the term "cycloalkylene" indicates a divalent group having one or more saturated rings in which all ring members are carbon, optionally substituted with one or more substituents where indicated, provided that the valence of the cycloalkylene group is not exceeded.

As used herein, when a definition is not otherwise provided, the term "oxycycloalkylene" indicates a cycloalkylene group in which any one or more methylene groups (—$CH_2$—) is substituted with an oxygen group (—O—), wherein the term "cycloalkylene" has the same meaning as described above.

As used herein, when a definition is not otherwise provided, the term "arylene" indicates a divalent group formed by the removal of two hydrogen atoms from one or more rings of an arene, wherein the hydrogen atoms may be removed from the same or different rings of the arene.

As used herein, when a definition is not otherwise provided, the term "oxyarylene" represents "-arylene-O—" or "—O-arylene-", wherein the term "arylene" has the same meaning as described above.

As used herein, when a definition is not otherwise provided, the term "alkylarylene" indicates an arylene group substituted with an alkylene group, wherein the terms "arylene" and "alkylene" have the same meaning as described above.

As used herein, when a definition is not otherwise provided, the term "arylalkylene" indicates an alkylene group substituted with an arylene group, wherein the terms "alkylene" and "arylene" have the same meaning as described above.

As used herein, when specific definition is not otherwise provided, the term "hetero" refers to one including 1 to 3 heteroatoms selected from N, O, S, Se, and P.

As used herein, when specific definition is not otherwise provided, the term "'heterocyclic group" refers to C1 to C20 heteroaryl group, for example C2 to C8 heteroaryl group, including 1 to 3 heteroatoms selected from N, O, S, Se, and P, or C1 to C20 heterocycloalkyl group, for example C3 to C8 heterocycloalkyl group, including 1 to 3 heteroatoms selected from N, O, S, Se, and P.

Hereinafter, a monomer according to an embodiment is described.

A monomer according to an embodiment is represented by Chemical Formula 1-1.

unsubstituted C3 to C20 heterocyclic group, a substituted or unsubstituted silyl group, a hydroxy group, a halogen, a nitro group, or a combination thereof, n and m are independently 0 or 1, p is an integer ranging from 1 to 3, a to f are independently integers ranging from 0 to 4, and a+b, c+d, and e+f are independently integers of less than or equal to 4.

Chemical Formula 1-1

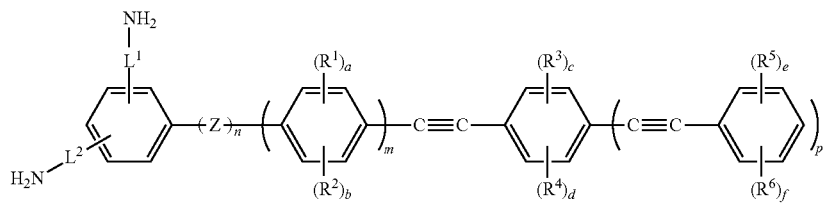

In Chemical Formula 1-1,

Z is —C=O—, —(C=O)O—, —O(C=O)—, —CH$_2$O—, —CF$_2$O—, —OC(=O)O—, —C≡C—, —CH=CH—, —CF=CF—, or —C(=O)NR$^a$—,

L$^1$ and L$^2$ are independently a single bond, a substituted or unsubstituted C1 to C20 alkylene group, a substituted or unsubstituted C1 to C20 oxyalkylene group, a substituted or unsubstituted C3 to C20 cycloalkylene group, a substituted or unsubstituted C3 to C20 oxycycloalkylene group, a substituted or unsubstituted C6 to C20 arylene group, a substituted or unsubstituted C6 to C20 oxyarylene group, a substituted or unsubstituted C3 to C20 divalent heterocyclic group, or a combination thereof, R$^1$ to R$^6$ and R$^a$ are independently hydrogen, a substituted or unsubstituted C1 to C20 alkyl group, a substituted or unsubstituted C1 to C20 alkoxy group, a substituted or unsubstituted C2 to C20 alkoxyalkyl group, a substituted or unsubstituted C1 to C20 fluoroalkyl group, a substituted or unsubstituted C3 to C20 cycloalkyl group, a substituted or unsubstituted C3 to C20 cycloalkyloxy group, a substituted or unsubstituted C4 to C20 cycloalkoxyalkyl group, a substituted or unsubstituted C6 to C20 aryl group, a substituted or unsubstituted C6 to C20 aryloxy group, a substituted or unsubstituted C7 to C20 arylalkyl group, a substituted or unsubstituted C7 to C20 aryloxyalkyl group, a substituted or For example, L$^1$ and L$^2$ may be independently a single bond, a substituted or unsubstituted C1 to C6 alkylene group, a substituted or unsubstituted C1 to C20 oxyalkylene group, a substituted or unsubstituted C3 to C8 cycloalkylene group, a substituted or unsubstituted C3 to C20 oxycycloalkylene group, a substituted or unsubstituted C6 to C12 arylene group, a substituted or unsubstituted C6 to C20 oxyarylene group, a substituted or unsubstituted C3 to C8 divalent heterocyclic group, or a combination thereof.

The monomer is a diamine compound including an acetylene group, and may be used as a reagent of a polyimide and/or polyamic acid.

The monomer may be, for example, represented by Chemical Formula 1-1a or 1-1b.

Chemical Formula 1-1a

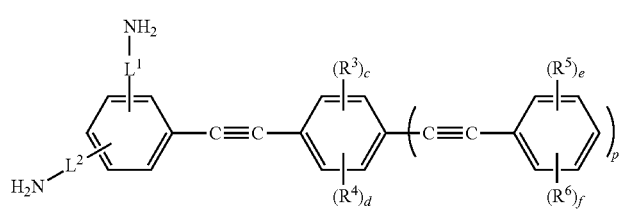

Chemical Formula 1-1b

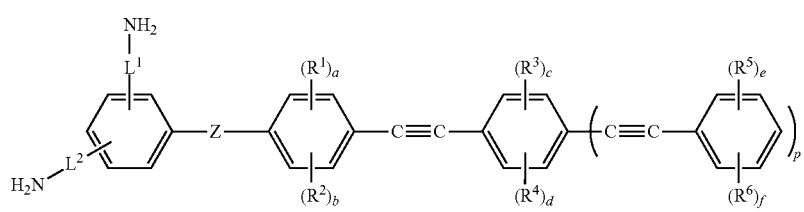

In Chemical Formulae 1-1a and 1-1b, Z, L$^1$, L$^2$, R$^1$ to R$^6$, n, m, p and a to f are the same as defined in Chemical Formula 1-1.

The monomer may be, for example, represented by Chemical Formula 1a or 1b.

Chemical Formula 1a

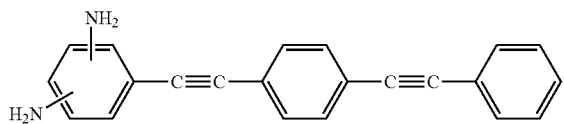

Chemical Formula 1b

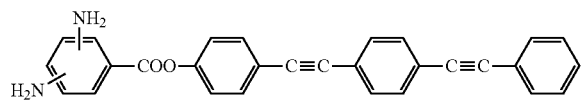

Hereinafter, a polymer according to an embodiment is described.

A polymer according to an embodiment is a reaction product of an anhydride and a diamine compound, and the polymer may include a moiety derived from a first diamine compound represented by Chemical Formula 1-1.

unsubstituted C1 to C20 alkoxy group, a substituted or unsubstituted C2 to C20 alkoxyalkyl group, a substituted or unsubstituted C1 to C20 fluoroalkyl group, a substituted or unsubstituted C3 to C20 cycloalkyl group, a substituted or unsubstituted C3 to C20 cycloalkyloxy group, a substituted or unsubstituted C4 to C20 cycloalkoxyalkyl group, a substituted or unsubstituted C6 to C20 aryl group, a substituted or unsubstituted C6 to C20 aryloxy group, a substituted or unsubstituted C7 to C20 arylalkyl group, a substituted or unsubstituted C7 to C20 aryloxyalkyl group, a substituted or unsubstituted C3 to C20 heterocyclic group, a substituted or unsubstituted silyl group, a hydroxy group, a halogen, a nitro group, or a combination thereof, n and m are independently 0 or 1, p is an integer ranging from 1 to 3, a to f are independently integers ranging from 0 to 4, and a+b, c+d, and e+f are independently integers of less than or equal to 4.

The polymer may be a polyimide, polyamic acid, or a combination thereof.

Chemical Formula 1-1

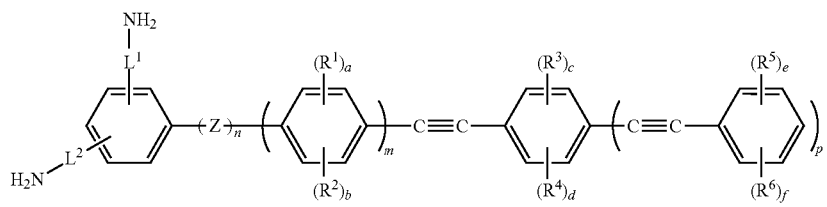

In Chemical Formula 1-1,

Z is —C=O—, —(C=O)O—, —O(C=O)—, —CH$_2$O—, —CF$_2$O—, —OC(=O)O—, —C≡C—, —CH=CH—, —CF=CF—, or —C(=O)NR$^a$—,

L$^1$ and L$^2$ are independently a single bond, a substituted or unsubstituted C1 to C20 alkylene group, a substituted or unsubstituted C1 to C20 oxyalkylene group, a substituted or unsubstituted C3 to C20 cycloalkylene group, a substituted or unsubstituted C3 to C20 oxycycloalkylene group, a substituted or unsubstituted C6 to C20 arylene group, a substituted or unsubstituted C6 to C20 oxyarylene group, a substituted or unsubstituted C3 to C20 divalent heterocyclic group, or a combination thereof, R$^1$ to R$^6$ and R$^a$ are independently hydrogen, a substituted or unsubstituted C1 to C20 alkyl group, a substituted or The polymer may include a main chain containing a polyimide, polyamic acid, or a combination thereof obtained by a reaction of an anhydride and a diamine compound, and a side chain including an acetylene group derived from the first diamine compound represented by Chemical Formula 1-1. The side chain including an acetylene group may be arranged in a substantially vertical direction with respect to the main chain, and may provide the polymer with predetermined modified optical properties.

The first diamine compound may be, for example, represented by Chemical Formula 1-1a or 1-1b.

Chemical Formula 1-1a

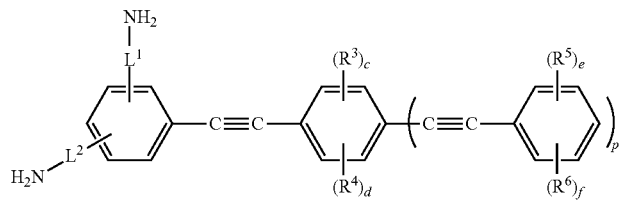

Chemical Formula 1-1b

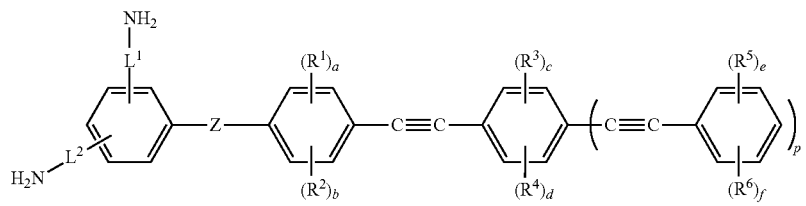

In Chemical Formulae 1-1a and 1-1b, Z, $L^2$, $R^1$ to $R^6$, n, m, p and a to f are the same as defined in Chemical Formula 1-1.

The first diamine compound may be, for example, represented by Chemical Formula 1a or 1b.

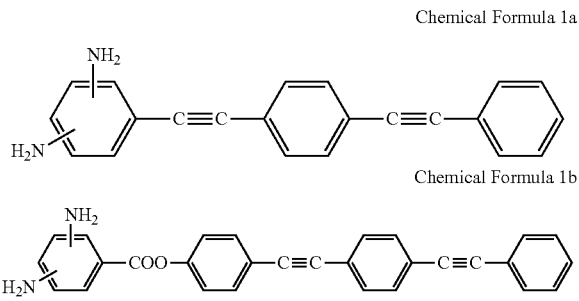

Chemical Formula 1a

Chemical Formula 1b

The diamine compound may further include a second diamine compound, which is different from the first diamine compound, in addition to the first diamine compound. One or more of the second diamine compound may be used.

The second diamine compound may, for example, include at least one selected from compounds of Group 1.

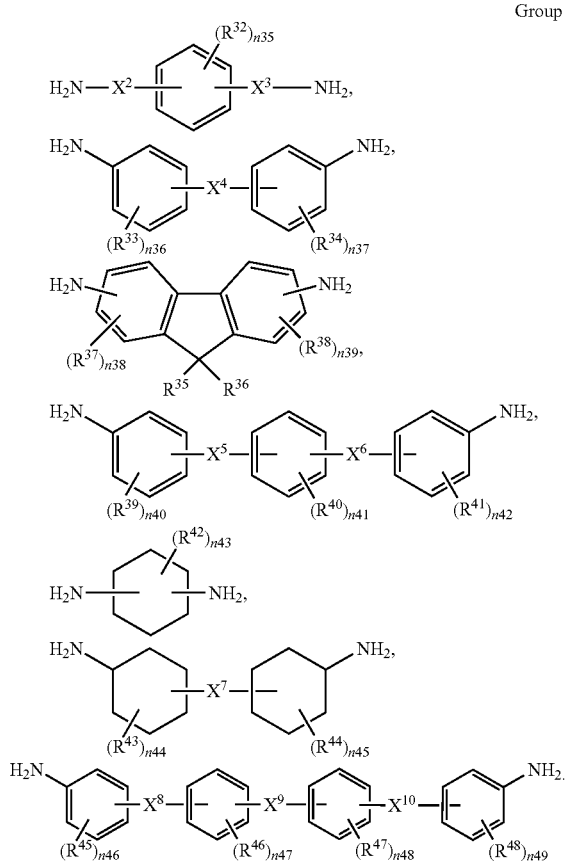

Group 1

In Group 1, $R^{32}$ to $R^{48}$ are independently hydrogen, a substituted or unsubstituted C1 to C20 alkyl group, a substituted or unsubstituted C1 to C20 alkoxy group, a substituted or unsubstituted C1 to C20 fluoroalkyl group, a substituted or unsubstituted C3 to C20 cycloalkyl group, a substituted or unsubstituted C3 to C20 heterocyclic group, a substituted or unsubstituted C3 to C20 cycloalkoxy group, a substituted or unsubstituted C6 to C20 aryl group, a substituted or unsubstituted C6 to C20 aryloxy group, a substituted or unsubstituted amine group, a substituted or unsubstituted C1 to C20 alkylamine group, a substituted or unsubstituted silyl group, a hydroxy group, a halogen, a nitro group, or a combination thereof, $X^2$ to $X^{10}$ are independently a single bond, a substituted or unsubstituted C1 to C20 alkylene group, a substituted or unsubstituted C3 to C20 cycloalkylene group, a substituted or unsubstituted C6 to C20 arylene group, a substituted or unsubstituted C3 to C20 divalent heterocyclic group, —$SO_2$—, —O—, —C(=O)—, —C(=O)O—, a group selected from Group 2, or a combination thereof, n35 to n37 and n40 to n49 are independently an integer ranging from 0 to 4, and n38 and n39 are independently an integer ranging from 0 to 3.

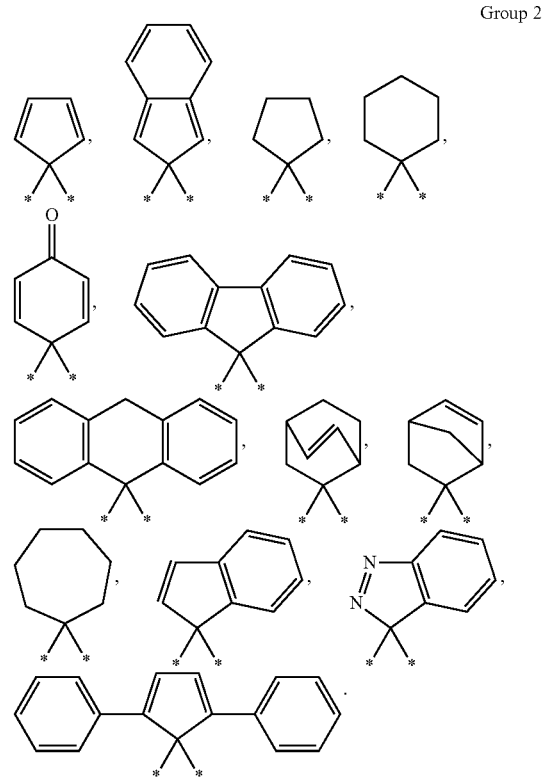

Group 2

The second diamine compound may include at least one selected from compounds of Group 3, but is not limited thereto.

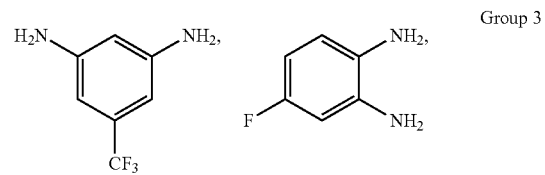

Group 3

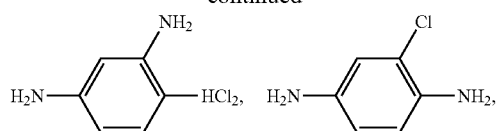
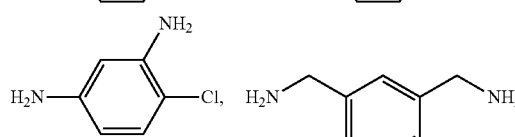
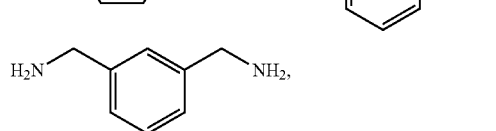
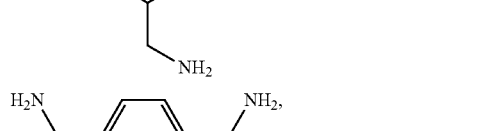
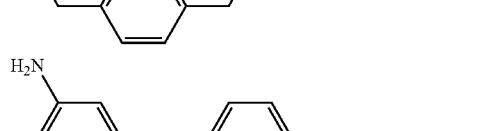
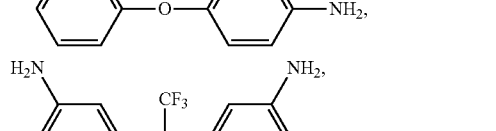
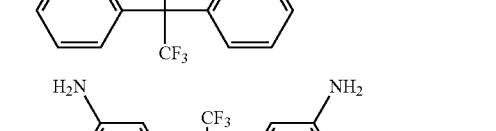
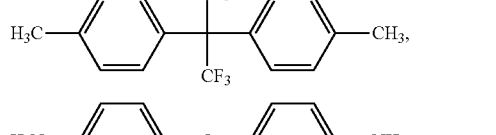
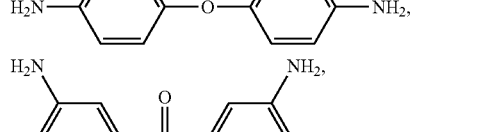
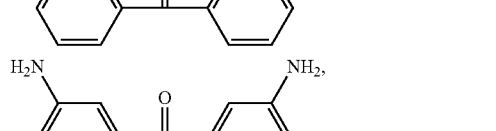
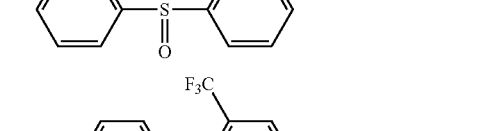
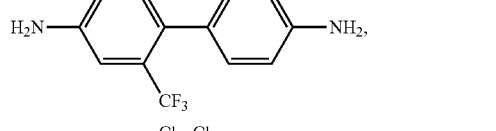
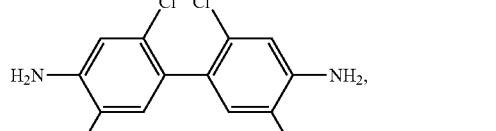
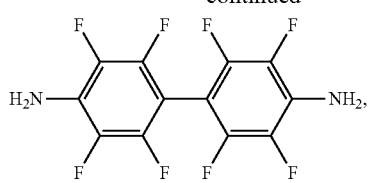
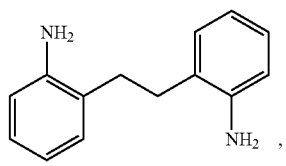
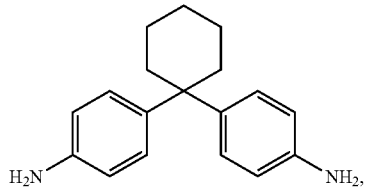
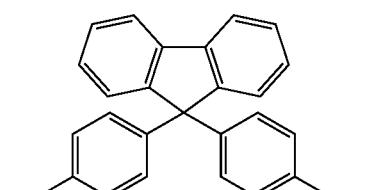
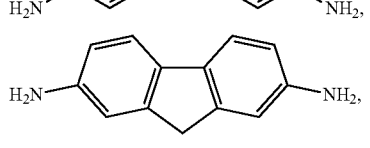
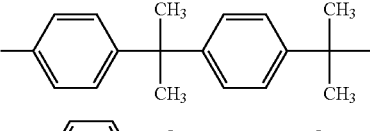
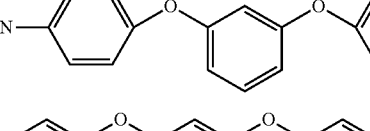
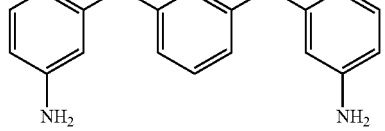
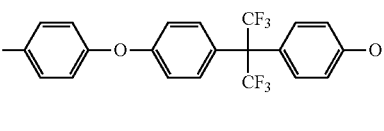
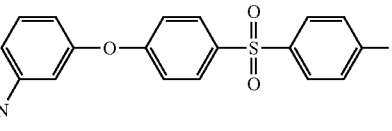
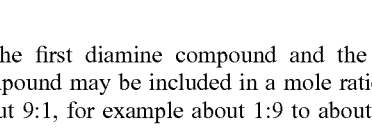
The first diamine compound and the second diamine compound may be included in a mole ratio of about 1:9 to about 9:1, for example about 1:9 to about 5:5.
The anhydride may be, for example, represented by Chemical Formula 2 or 3.

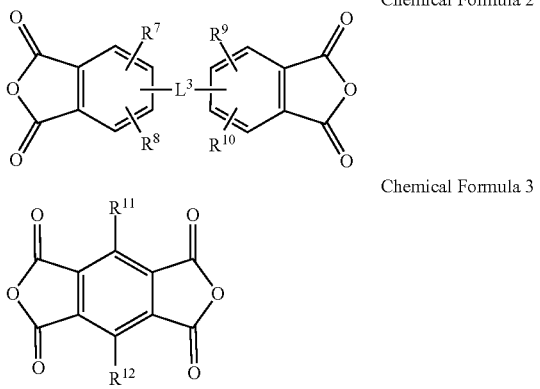

Chemical Formula 2

Chemical Formula 3

In Chemical Formula 2 or 3, $L^3$ is a single bond, a substituted or unsubstituted C1 to C20 alkylene group, a substituted or unsubstituted C1 to C20 oxyalkylene group, a substituted or unsubstituted C3 to C20 cycloalkylene group, a substituted or unsubstituted C3 to C20 oxycycloalkylene group, a substituted or unsubstituted C6 to C20 arylene group, a substituted or unsubstituted C6 to C20 oxyarylene group, a substituted or unsubstituted C3 to C20 divalent heterocyclic group, —O—, —C(=O)—, —C(=O)O—, —SO$_2$—, —C(=O)NR$^b$—, or a combination thereof, and $R^7$ to $R^{12}$ and $R^b$ are independently hydrogen, a substituted or unsubstituted C1 to C20 alkyl group, a substituted or unsubstituted C1 to C20 alkoxy group, a substituted or unsubstituted C2 to C20 alkoxyalkyl group, a substituted or unsubstituted C1 to C20 fluoroalkyl group, a substituted or unsubstituted C3 to C20 cycloalkyl group, a substituted or unsubstituted C3 to C20 cycloalkyloxy group, a substituted or unsubstituted C4 to C20 cycloalkoxyalkyl group, a substituted or unsubstituted C6 to C20 aryl group, a substituted or unsubstituted C6 to C20 aryloxy group, a substituted or unsubstituted C7 to C20 arylalkyl group, a substituted or unsubstituted C7 to C20 aryloxyalkyl group, a substituted or unsubstituted C3 to C20 heterocyclic group, a substituted or unsubstituted silyl group, a hydroxy group, a halogen, a nitro group, or a combination thereof.

The anhydride may include, for example, 2,3,3',4'-biphenyltetracarboxylic dianhydride, 2,3,3',4'-diphenylsulfone tetracarboxylic dianhydride, 3,4'-oxydiphthalic anhydride, 3,3',4,4'-biphenyl tetracarboxylic dianhydride (BPDA), bicyclo[2.2.2]oct-7-ene-2,3,5,6-tetracarboxylic dianhydride (BTDA), 3,3',4,4'-diphenylsulfone tetracarboxylic dianhydride (DSDA), 4,4'-(hexafluoroisopropylidene)diphthalic anhydride (6FDA), 4,4'-oxydiphthalic anhydride (ODPA), pyromellitic dianhydride (PMDA), 4-(2,5-dioxotetrahydrofuran-3-yl)-1,2,3,4-tetrahydronaphthalene-1,2-dicarboxylic anhydride (DTDA), or a combination thereof, but is not limited thereto.

The anhydride and the diamine compound may be, for example, included in a mole ratio of about 1:9 to about 9:1, for example about 3:7 to about 7:3, and in another example about 5:5.

The polymer may be, for example, prepared in a form of a thin film, and may be used as a polymer film. The polymer film may be, for example, transparent, and may be used for articles requiring transparency. The polymer film may be, for example, used as a substrate, a protective film, an optical film, a dielectric layer, an insulation layer, an adhesive layer, and the like.

Hereinafter, a compensation film according to an embodiment is provided.

A compensation film according to an embodiment includes a polymer, which is a reaction product of an anhydride and a diamine compound, wherein the polymer includes a side chain including at least one acetylene group.

The polymer may be a polyimide, polyamic acid, or a combination thereof.

The polymer may include a main chain containing a polyimide, polyamic acid, or a combination thereof obtained by a reaction of an anhydride and a diamine compound, and a side chain including at least one acetylene group. The side chain of the polymer may be arranged in a substantially vertical direction with respect to the main chain of the polymer, and may modify light absorption characteristics depending on a refractive index and a wavelength, and thus a phase delay due to the presence of at least one acetylene group in the side chain. For example, the polymer may adjust a refractive index ($n_e$) in a main chain direction and a refractive index ($n_o$) in a side chain direction, and thus control birefringence depending on a wavelength.

The side chain of the polymer may be derived from the diamine compound, and the diamine compound may further include at least one substituted or unsubstituted arylene group in addition to the above at least one acetylene group.

One or more of the diamine compound may be used, and the diamine compound may include, for example, a first diamine compound represented by Chemical Formula 1-2.

Chemical Formula 1-2

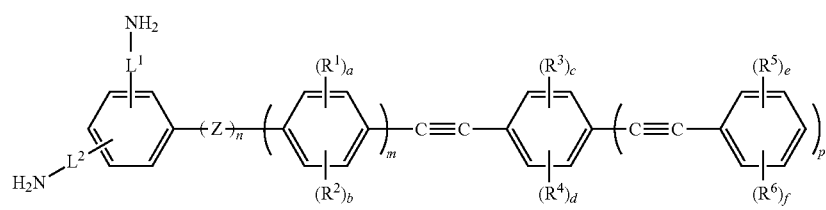

In Chemical Formula 1-2,

Z is —C=O—, —(C=O)O—, —O(C=O)—, —CH$_2$O—, —CF$_2$O—, —OC(=O)O—, —C≡C—, —CH=CH—, —CF=CF—, or —C(=O)NR$^a$—, $L^1$ and $L^2$ are independently a single bond, a substituted or unsubstituted C1 to C20 alkylene group, a substituted or unsubstituted C1 to C20 oxyalkylene group, a substituted or unsubstituted C3 to C20 cycloalkylene group, a substituted or unsubstituted C3 to C20 oxycycloalkylene group, a substituted or unsubstituted C6 to C20 arylene group, a substituted or unsubstituted C6 to C20 oxyarylene group, a substituted or unsubstituted C3 to C20 divalent heterocyclic group, or a combination thereof, $R^1$ to $R^6$ and $R^a$ are independently hydrogen, a substituted or unsubstituted C1 to C20 alkyl group, a substituted or unsubstituted C1 to C20 alkoxy group, a substituted or unsubstituted C2 to C20 alkoxyalkyl group, a substituted or unsubstituted C1 to C20 fluoroalkyl group, a substituted or unsubstituted C3 to C20 cycloalkyl group, a substituted or unsubstituted C3 to C20 cycloalkyloxy group, a substituted or unsubstituted C4 to C20 cycloalkoxyalkyl group, a substituted or unsubstituted C6 to C20 aryl group, a substituted or unsubstituted C6 to C20 aryloxy group, a substituted or unsubstituted C7 to C20 arylalkyl group, a substituted or unsubstituted C7 to C20 aryloxyalkyl group, a substituted or unsubstituted C3 to C20 heterocyclic group, a substituted or unsubstituted silyl group, a hydroxy group, a halogen, a nitro group, or a combination thereof, n and m are independently 0 or 1, p is an integer ranging from 0 to 3, a to f are independently integers ranging from 0 to 4, and a+b, c+d, and e+f are independently integers of less than or equal to 4.

The first diamine derivative may be, for example, represented by Chemical Formula 1-2a or 1-2b.

Chemical Formula 1-2a

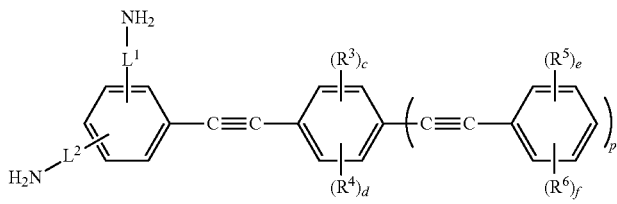

Chemical Formula 1-2b

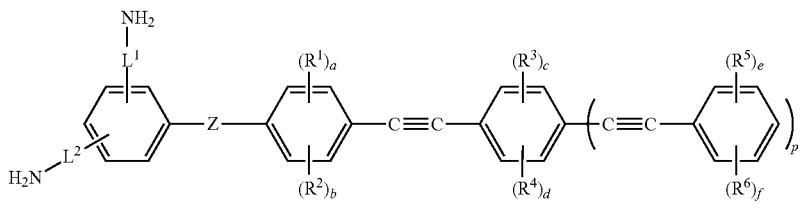

In Chemical Formulae 1-2a and 1-2b, Z, $L^2$, $R^1$ to $R^6$, n, m, p and a to f are the same as defined in Chemical Formula 1-2.

The first diamine compound may be, for example, represented by one of Chemical Formulae 1a to 1d, but is not limited thereto.

Chemical Formula 1a

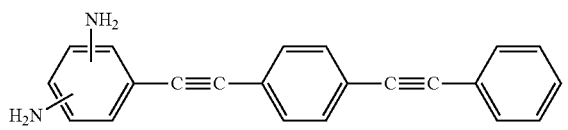

Chemical Formula 1b

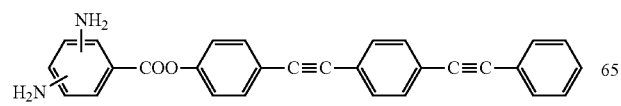

Chemical Formula 1c

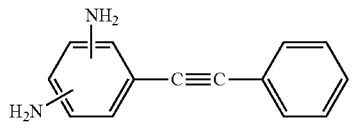

Chemical Formula 1d

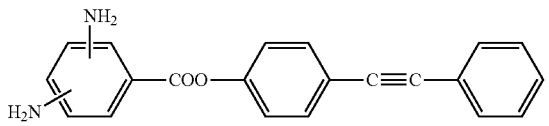

The diamine compound may further include a second diamine compound, which is different from the first diamine compound, in addition to the first diamine compound. One or more of the second diamine compound may be used.

The second diamine compound may, for example, include at least one selected from compounds of Group 1.

Group 1

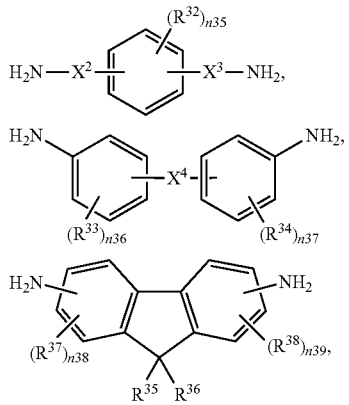

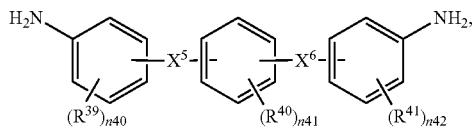

-continued

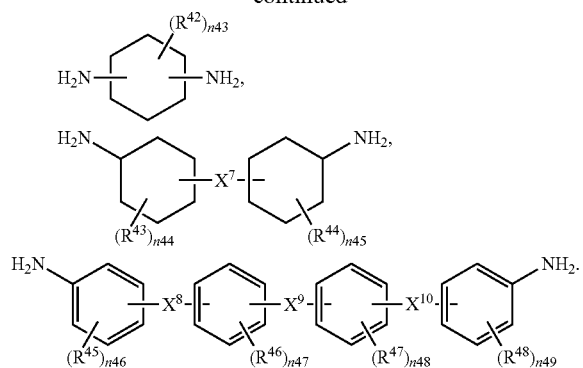

In Group 1,

R$^{32}$ to R$^{48}$ are independently hydrogen, a substituted or unsubstituted C1 to C20 alkyl group, a substituted or unsubstituted C1 to C20 alkoxy group, a substituted or unsubstituted C1 to C20 fluoroalkyl group, a substituted or unsubstituted C3 to C20 cycloalkyl group, a substituted or unsubstituted C3 to C20 heterocyclic group, a substituted or unsubstituted C3 to C20 cycloalkoxy group, a substituted or unsubstituted C6 to C20 aryl group, a substituted or unsubstituted C6 to C20 aryloxy group, a substituted or unsubstituted amine group, a substituted or unsubstituted C1 to C20 alkylamine group, a substituted or unsubstituted silyl group, a hydroxy group, a halogen, a nitro group, or a combination thereof, X$^2$ to X$^{10}$ are independently a single bond, a substituted or unsubstituted C1 to C20 alkylene group, a substituted or unsubstituted C3 to C20 cycloalkylene group, a substituted or unsubstituted C6 to C20 arylene group, a substituted or unsubstituted C3 to C20 divalent heterocyclic group, —SO$_2$—, —O—, —C(=O)—, —O(=O)O—, a group selected from Group 2, or a combination thereof, n35 to n37 and n40 to n49 are independently an integer ranging from 0 to 4, and n38 and n39 are independently an integer ranging from 0 to 3.

Group 2

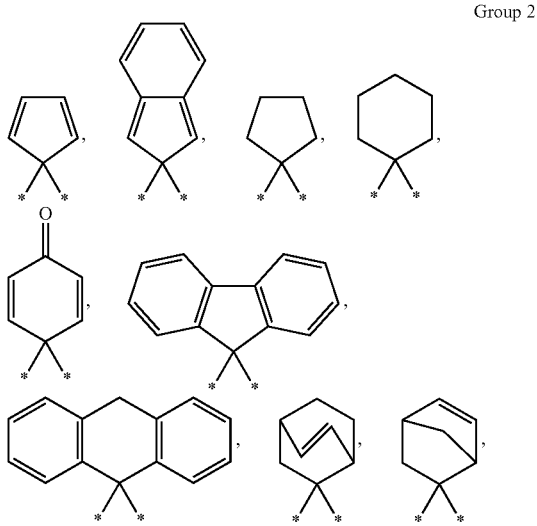

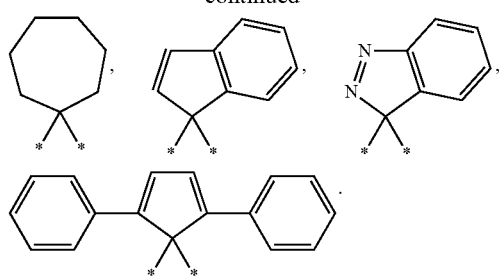

The second diamine compound may include at least one selected from compounds of Group 3, but is not limited thereto.

Group 3

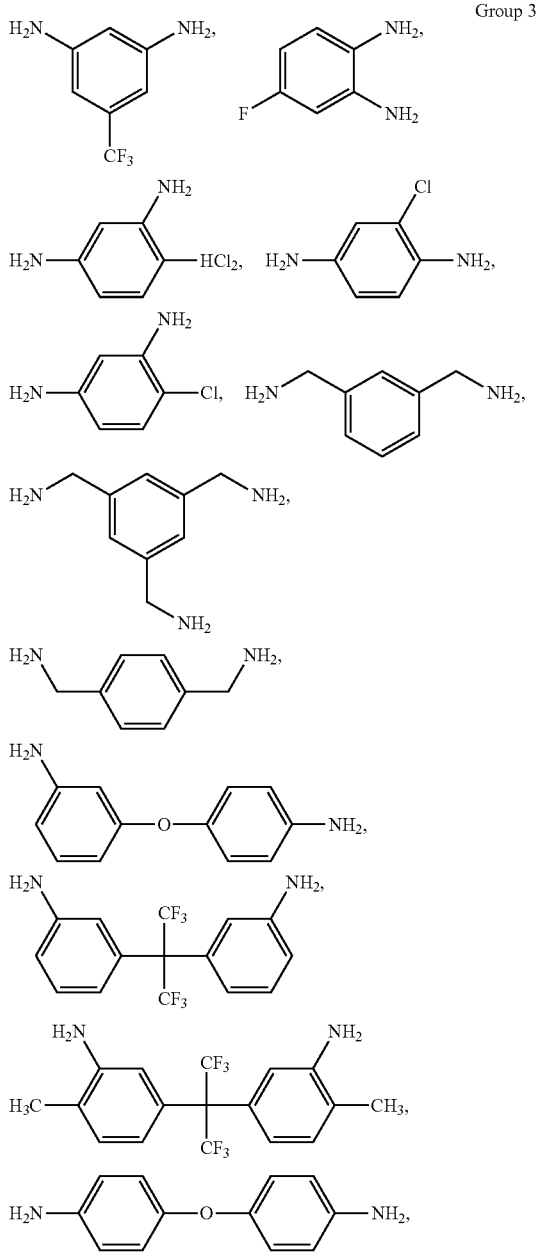

-continued

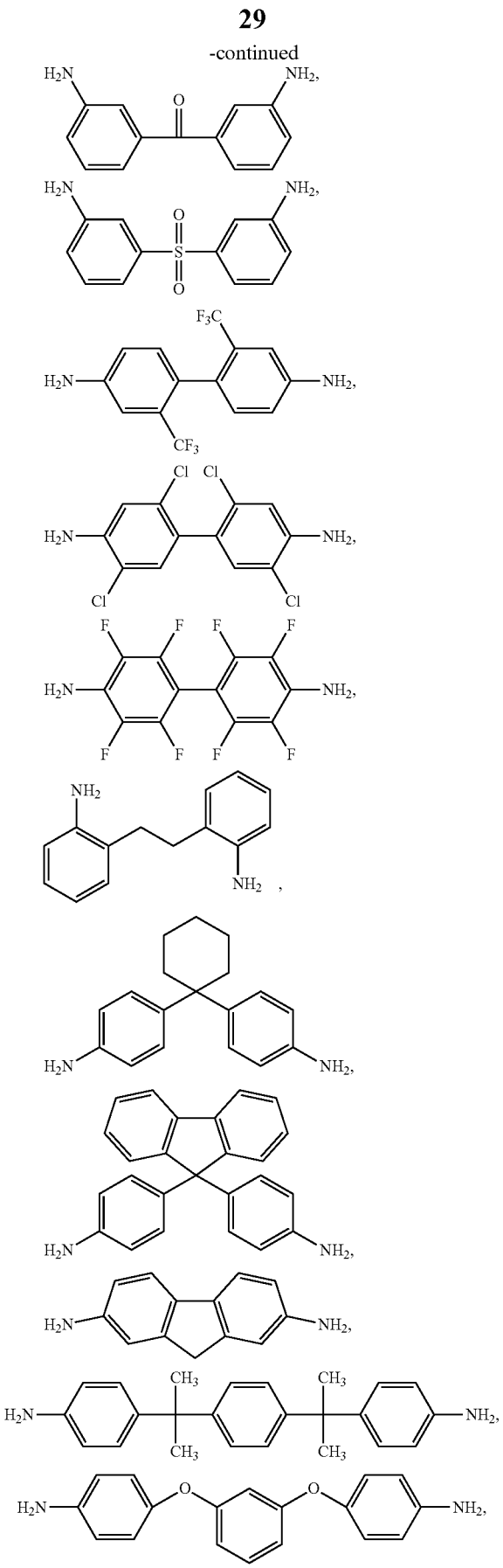

-continued

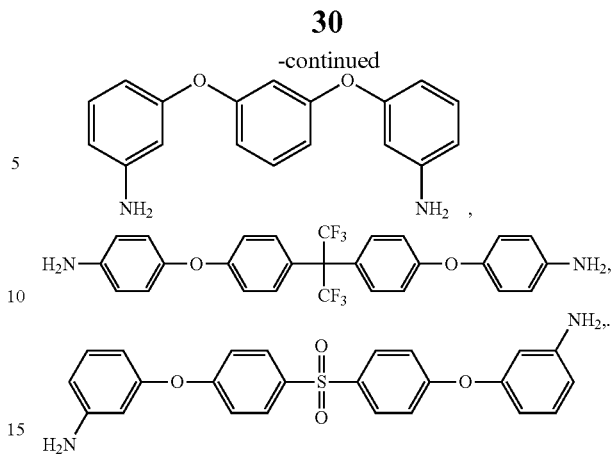

The first diamine compound and the second diamine compound may be included in a mole ratio of about 1:9 to about 9:1, for example about 1:9 to about 5:5.

The anhydride may be, for example, represented by Chemical Formula 2 or 3.

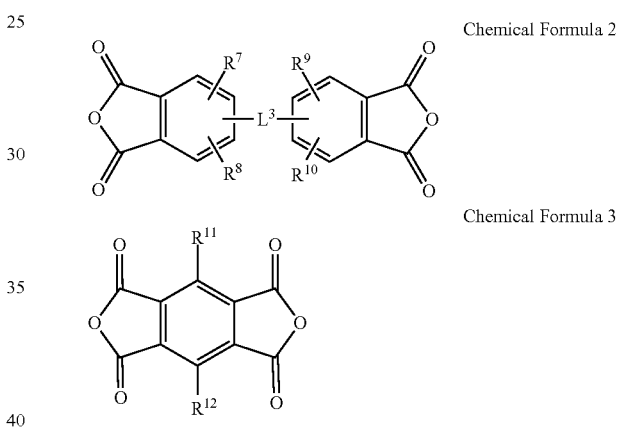

In Chemical Formula 2 or 3, $L^3$ is a single bond, a substituted or unsubstituted C1 to C20 alkylene group, a substituted or unsubstituted C1 to C20 oxyalkylene group, a substituted or unsubstituted C3 to C20 cycloalkylene group, a substituted or unsubstituted C3 to C20 oxycycloalkylene group, a substituted or unsubstituted C6 to C20 arylene group, a substituted or unsubstituted C6 to C20 oxyarylene group, a substituted or unsubstituted C3 to C20 divalent heterocyclic group, —O—, —C(=O)—, —C(=O)O—, —SO$_2$—, —C(=O)NR$^b$—, or a combination thereof, and $R^7$ to $R^{12}$ and $R^b$ are independently hydrogen, a substituted or unsubstituted C1 to C20 alkyl group, a substituted or unsubstituted C1 to C20 alkoxy group, a substituted or unsubstituted C2 to C20 alkoxyalkyl group, a substituted or unsubstituted C1 to C20 fluoroalkyl group, a substituted or unsubstituted C3 to C20 cycloalkyl group, a substituted or unsubstituted C3 to C20 cycloalkyloxy group, a substituted or unsubstituted C4 to C20 cycloalkoxyalkyl group, a substituted or unsubstituted C6 to C20 aryl group, a substituted or unsubstituted C6 to C20 aryloxy group, a substituted or unsubstituted C7 to C20 arylalkyl group, a substituted or unsubstituted C7 to C20 aryloxyalkyl group, a substituted or unsubstituted C3 to C20 heterocyclic group, a substituted or unsubstituted silyl group, a hydroxy group, a halogen, a nitro group, or a combination thereof.

The anhydride may include, for example, 2,3,3',4'-biphenyltetracarboxylic dianhydride, 2,3,3',4'-diphenylsulfone tetracarboxylic dianhydride, 3,4'-oxydiphthalic anhydride, 3,3',4,4'-biphenyl tetracarboxylic dianhydride (BPDA), bicyclo[2.2.2]oct-7-ene-2,3,5,6-tetracarboxylic dianhydride (BTDA), 3,3',4,4'-diphenylsulfone tetracarboxylic dianhydride (DSDA), 4,4'-(hexafluoroisopropylidene)diphthalic anhydride (6FDA), 4,4'-oxydiphthalic anhydride (ODPA), pyromellitic dianhydride (PMDA), 4-(2,5-dioxotetrahydrofuran-3-yl)-1,2,3,4-tetrahydronaphthalene-1,2-dicarboxylic anhydride (DTDA), or a combination thereof, but is not limited thereto.

The anhydride and the diamine compound may be, for example, included in a mole ratio of about 1:9 to about 9:1, for example about 3:7 to about 7:3, and in another example about 5:5.

The compensation film may be, for example, elongated in a uniaxial direction.

As described above, the compensation film may have modified light absorption characteristics depending on a refractive index and a wavelength due to the polymer having at least one acetylene group in the side chain, and thus may have desirable phase delay characteristics by varying the number of the acetylene groups and length of the side chain.

For example, the compensation film may have retardation ranging from about 110 nanometers (nm) to about 160 nm at a wavelength of about 550 nm (hereinafter called a "reference wavelength"). Herein, the retardation may be in-plane retardation or thickness direction retardation. The retardation of the compensation film at a wavelength of about 550 nm may be, for example, in a range of about 120 nm to about 150 nm within the above broader range.

The retardation of the compensation film may be the same or different depending on a wavelength.

For example, the compensation film may have a reverse wavelength dispersion phase delay in which retardation regarding light at a long wavelength is greater than retardation regarding light at a short wavelength, and herein, the retardation (R) of the compensation film regarding light at a wavelength of about 450 nm, about 550 nm, and about 650 nm may satisfy Relationship Equation 1 or 2.

$R(450 \text{ nm}) \leq R(550 \text{ nm}) < R(650 \text{ nm})$  Relationship Equation 1

$R(450 \text{ nm}) < R(550 \text{ nm}) \leq R(650 \text{ nm})$  Relationship Equation 2

For example, the compensation film may have a normal wavelength dispersion phase delay in which retardation regarding light at a long wavelength is less than retardation regarding light at a short wavelength, and herein, the retardation (R) of the compensation film regarding light at a wavelength of about 450 nm, about 550 nm, and about 650 nm may satisfy Relationship Equation 3 or 4.

$R(450 \text{ nm}) \geq R(550 \text{ nm}) > R(650 \text{ nm})$  Relationship Equation 3

$R(450 \text{ nm}) > R(550 \text{ nm}) \leq R(650 \text{ nm})$  Relationship Equation 4

For example, the compensation film may have a flat wavelength dispersion phase delay in which retardation regarding light at a long wavelength is substantially equal to retardation regarding light at a short wavelength, and herein, the retardation (R) of the compensation film regarding light at a wavelength of about 450 nm, about 550 nm, and about 650 nm may satisfy Relationship Equation 5.

$R(450 \text{ nm}) = R(550 \text{ nm}) = R(650 \text{ nm})$  Relationship Equation 5

The compensation film may have high birefringence and thus a relatively low thickness. The compensation film may have, for example, a thickness of about 3 micrometers (μm) to about 100 μm, for example, a thickness of about 5 μm to about 70 μm, and in another example, a thickness of about 5 μm to about 30 μm.

The compensation film includes a substantially transparent polymer, which may be used as a substrate, and accordingly, a separate substrate may be omitted beneath the compensation film. Accordingly, the compensation film may be much thinner. The compensation film may be effectively applied to a flexible display device such as a foldable display device or a bendable display device, and thus improve optical properties and display characteristics.

The compensation film may be, for example, manufactured by a method including providing a composition, transforming the composition into a thin film, and curing the thin film.

The composition may include an anhydride, a diamine compound, and a solvent. The anhydride and diamine compound are the same as described above. The solvent may be, for example, an aprotic polar solvent, for example a sulfoxide-containing solvent such as dimethylsulfoxide and diethylsulfoxide, a formamide-containing solvent such as N,N-dimethylformamide and N,N-diethylformamide, an acetamide-containing solvent such as N,N-dimethylacetamide, N,N-di methylmethoxyacetamide, and N,N-diethylacetamide, a pyrrolidone-containing solvent such as N-methyl-2-pyrrolidone (NMP), N-acetyl-2-pyrrolidone, and N-vinyl-2-pyrrolidone, a halogenated phenol such as o-cresol, m-cresol, p-cresol, and xylenol, and a phenol-containing solvent such as catechol, hexamethylphosphoramide, γ-butyrolactone, tetrahydrothiophene dioxide, N-methyl-δ-caprolactam, N,N,N',N'-tetramethylurea, or a mixture thereof, but is not limited thereto.

The anhydride and the diamine compound may be, for example, included in a mole ratio of about 1:9 to about 9:1, for example about 3:7 to about 7:3, and in another example about 5:5.

The anhydride and the diamine compound may be included in an amount of about 10 to about 80 percent by weight (wt %), for example about 30 to about 60 wt %, based on the total amount of the composition. The solvent may be included in a balance amount except the anhydride and the diamine compound in the composition.

The composition may be, for example, coated by spin coating, slit coating, inkjet coating, dip coating, and the like, but is not limited thereto.

The curing may be, for example, performed at about 50 to about 120° C., for example about 70 to about 100° C.

The compensation film may be, for example, elongated in a uniaxial direction. The compensation film may be, for example, elongated at an elongation rate of about 200% to about 1,000% at a temperature of about 50° C. to about 500° C. Herein the elongation rate refers to a length ratio of after the elongation to before the elongation of the compensation film, and means the elongation extent of the compensation film after uniaxial elongation.

The compensation film may be used alone or with another compensation film.

The compensation film may be used with a polarization film to provide an optical film for preventing reflection of external light of a display device. The optical film may be, for example, an antireflective film, but is not limited thereto.

Figure 2:
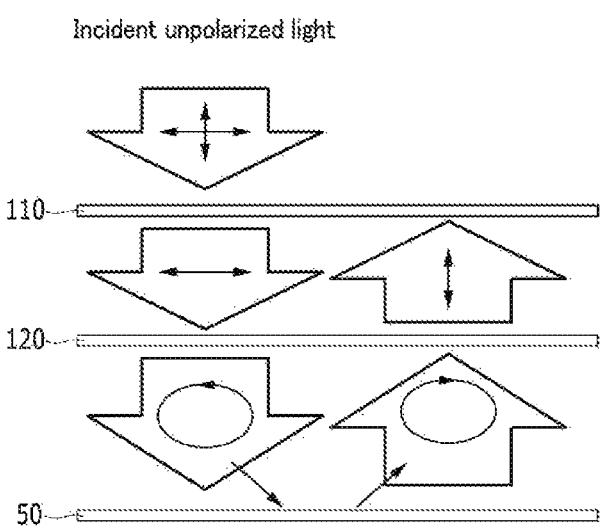
FIG. 2 is a schematic view showing the anti-reflection principle of an optical film according to an embodiment.
Figure 3:
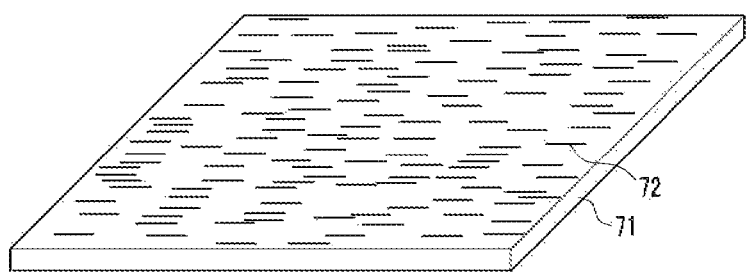
FIG. 3 is a schematic view showing an example of a polarization film.

FIG. 1 is a schematic cross-sectional view showing an optical film according to an embodiment, FIG. 2 is a schematic view showing the anti-reflection principle of an optical film according to an embodiment, and FIG. 3 is a schematic view showing an example of a polarization film.

Referring to FIG. 1, an optical film 100 according to an embodiment includes a polarization film 110 and a compensation film 120. The compensation film 120 may circularly polarize light passing through the polarization film 110 and thus cause retardation and have an influence on reflection and/or absorption of the light.

For example, the optical film 100 may be disposed on one side or both sides of a display device, and particularly, on the screen side of the display device, and thus may prevent reflection of light flowing in from the outside (hereinafter referred to as "reflection of external light"). Therefore, the optical film 100 may prevent visibility deterioration due to the reflection of external light.

FIG. 2 is a schematic view showing the external light anti-reflection principle of an optical film according to an embodiment.

Referring to FIG. 2, while the incident unpolarized light having entered from the outside is passed through the polarization film 110, and the polarized light is shifted into circularly polarized light by passing through the compensation film 120, only a first polarized perpendicular component, which is one polarized perpendicular component of two polarized perpendicular components, is transmitted. While the circularly polarized light is reflected in a display panel 50 including a substrate, an electrode, and so on, is changed in the circular polarization direction, and is passed through the compensation film 120 again, only a second polarized perpendicular component, which is the other polarized perpendicular component of the two polarized perpendicular components, may be transmitted. As the second polarized perpendicular component is not passed through the polarization film 110, and light does not exit to the outside, an effect of preventing the external light reflection may be provided.

Referring to FIG. 3, the polarization film 110 has a self-integrated structure which is made of a melt blend of a polymer 71 and a dichroic dye 72.

The polymer 71 may be, for example, a hydrophobic polymer, for example a polyolefin such as polyethylene (PE), polypropylene (PP), and a copolymer thereof; a polyamide such as nylon and an aromatic polyamide; a polyester such as polyethylene terephthalate (PET), glycol modified polyethylene terephthalate (PETG), and polyethylene naphthalate (PEN); a polyacrylate such as polymethyl(meth) acrylate; a polystyrene such as polystyrene (PS) and an acrylonitrile-styrene copolymer; a polycarbonate; a vinyl chloride type polymer; a polyimide; a polysulfone resin; a polyethersulfone; a polyether-etherketone; a polyphenylene sulfide; a vinyl alcohol type polymer; a vinylidene chloride type polymer; a vinyl butyral type polymer; an allylic polymer; a polyoxymethylene; an epoxy polymer; a copolymer thereof; or a combination thereof.

Among them, the polymer 71 may be, for example, a polyolefin, a polyamide, a polyester, a polyacrylate, a polystyrene, a copolymer thereof, or a combination thereof, and in another example, polyethylene (PE), polypropylene (PP), polyethylene terephthalate (PET), glycol modified polyethylene terephthalate (PETG), polyethylene naphthalate (PEN), nylon, a copolymer thereof, or a combination thereof.

The polymer 71 may be a polyolefin. The polyolefin may be, for example, a mixture of at least two selected from polyethylene (PE), polypropylene (PP), and a copolymer of polyethylene and polypropylene (PE-PP), and in another example, a mixture of polypropylene (PP) and a polyethylene-polypropylene copolymer (PE-PP).

The polymer 71 may have transmittance of greater than or equal to about 85% in a wavelength region of about 400 nm to about 780 nm. The polymer 71 is elongated in a uniaxial direction. The uniaxial direction may be the same as a length direction of the dichroic dye 72.

The dichroic dye 72 is dispersed into the polymer 71, and is aligned in the elongation direction of the polymer 71. The dichroic dye 72 may transmit one perpendicular polarization component of two perpendicular polarization components in a predetermined wavelength region.

The dichroic dye 72 may be included in an amount of about 0.01 to about 5 parts by weight, based on 100 parts by weight of the polymer 71. While not wishing to be bound by theory, it is understood that within the above range, sufficient polarization characteristics may be obtained without deteriorating transmittance of a polarization film. Within the above broader range, the dichroic dye 72 may be included in an amount of about 0.05 to about 1 part by weight, based on 100 parts by weight of the polymer 71.

The polarization film 110 may have a relatively low thickness of less than or equal to about 100 μm, for example about 30 μm to about 95 μm. While not wishing to be bound by theory, it is understood that when the polarization film 110 has a thickness within the range, it may be significantly thinner than a polarizing plate requiring a protective layer such as triacetyl cellulose (TAC), and may contribute to realizing a thin display device.

The compensation film 120 is the same as described above.

The optical film 100 may further include a correction layer (not shown) positioned on one side of the compensation film 120. The correction layer may be, for example, a color shift resistant layer, but is not limited thereto.

The optical film 100 may further include a light blocking layer (not shown) extended along the edge. The light blocking layer may be formed in a strip along the circumference of the optical film 100, and for example, may be positioned between the polarization film 110 and the compensation film 120. The light blocking layer may include an opaque material, for example, a black material. For example, the light blocking layer may be made of a black ink.

The optical film 100 may be applied to various display devices.

A display device according to an embodiment includes a display panel and an optical film positioned on the display panel. The display panel may be a liquid crystal display panel or an organic light emitting display panel, but is not limited thereto.

Hereinafter, an organic light emitting diode device is described as an example of a display device.

Figure 4:
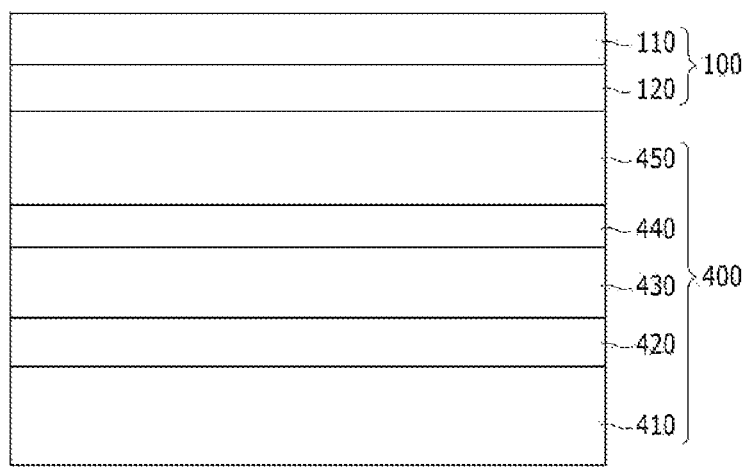
FIG. 4 is a schematic cross-sectional view showing an organic light emitting diode (OLED) device according to an embodiment.

FIG. 4 is a schematic cross-sectional view showing an organic light emitting diode (OLED) device according to an embodiment.

Referring to FIG. 4, the organic light emitting diode device according to an embodiment includes an organic light emitting display panel 400 and an optical film 100 positioned on the organic light emitting display panel 400.

The organic light emitting display panel 400 may include a base substrate 410, a lower electrode 420, an organic emission layer 430, an upper electrode 440, and an encapsulation substrate 450.

The base substrate 410 may be made of glass or plastic.

At least one of the lower electrode 420 and the upper electrode 440 may be an anode, and the other may be a cathode. The anode is an electrode injected with holes, and it may be made of a transparent conductive material having a high work function to transmit the emitted light to the outside, for example, ITO or IZO. The cathode is an electrode injected with electrons, and it may be made of a conductive material having a low work function without affecting the organic material, and may be selected from, for example, aluminum (Al), calcium (Ca), and barium (Ba).

The organic emission layer 430 includes an organic material which may emit light when a voltage to the lower electrode 420 and the upper electrode 440 is applied.

An auxiliary layer (not shown) may be further provided between the lower electrode 420 and the organic emission layer 430, and between the upper electrode 440 and the organic emission layer 430. The auxiliary layer is used to balance electrons and holes, and may include a hole transport layer, a hole injection layer (HIL), an electron injection layer (EIL), and an electron transporting layer.

The encapsulation substrate 450 may be made of glass, metal, or a polymer, and may seal the lower electrode 420, the organic emission layer 430, and the upper electrode 440 to prevent moisture and/or oxygen inflow from the outside.

The optical film 100 may be disposed on the light-emitting side. For example, in the case of a bottom emission structure emitting light at the side of the base substrate 410, the optical film 100 may be disposed on the exterior side of the base substrate 410, while in the case of a top emission structure emitting light at the side of the encapsulation substrate 450, the optical film 100 may be disposed on the exterior side of the encapsulation substrate 450.

The optical film 100 includes the integrated polarization film 110 and the integrated compensation film 120. The polarization film 110 and the compensation film 120 are respectively the same as described above, and may prevent a display device from having visibility deterioration caused by light inflowing from the outside after passing the polarization film 110 and being reflected by a metal such as an electrode and the like in the organic light emitting display panel 400. Accordingly, display characteristics of the organic light emitting diode device may be improved.

Hereinafter, a liquid crystal display (LCD) device is described as an example of the display device.

Figure 5:
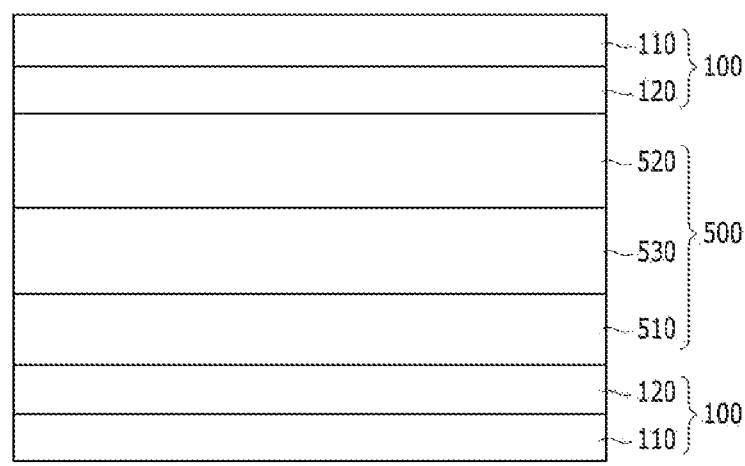
FIG. 5 is a schematic cross-sectional view showing a liquid crystal display (LCD) device according to an embodiment.

FIG. 5 is a schematic cross-sectional view showing a liquid crystal display (LCD) device according to an embodiment.

Referring to FIG. 5, the liquid crystal display (LCD) according to an embodiment includes a liquid crystal display panel 500, and an optical film 100 positioned on the liquid crystal panel 500.

The liquid crystal panel 500 may be a twist nematic (TN) mode panel, a patterned vertical alignment (PVA) mode panel, an in-plane switching (IPS) mode panel, an optically compensated bend (OCB) mode panel, or the like.

The liquid crystal panel 500 may include a first display panel 510, a second display panel 520, and a liquid crystal layer 530 interposed between the first display panel 510 and the second display panel 520.

The first display panel 510 may include, for example, a thin film transistor (not shown) formed on a substrate (not shown) and a first electric field generating electrode (not shown) connected to the same, and the second display panel 520 may include, for example, a color filter (not shown) formed on a substrate (not shown) and a second electric field generating electrode (not shown). However, it is not limited thereto, and the color filter may be included in the first display panel 510, while the first electric field generating electrode and the second electric field generating electrode may be disposed on the first display panel 510 together therewith.

The liquid crystal layer 530 may include a plurality of liquid crystal molecules. The liquid crystal molecules may have positive or negative dielectric anisotropy. In the case of the liquid crystal molecules having positive dielectric anisotropy, the major axes thereof may be aligned substantially parallel to the surface of the first display panel 510 and the second display panel 520 when an electric field is not applied, and the major axes may be aligned substantially perpendicular to the surface of the first display panel 510 and second display panel 520 when an electric field is applied. On the other hand, in the case of the liquid crystal molecules having negative dielectric anisotropy, the major axes may be aligned substantially perpendicular to the surface of the first display panel 510 and the second display panel 520 when an electric field is not applied, and the major axes may be aligned substantially parallel to the surface of the first display panel 510 and the second display panel 520 when an electric field is applied.

The optical film 100 may be disposed on the outside of the liquid crystal panel 500. Although the optical film 100 is shown to be provided on both the lower part and the upper part of the liquid crystal panel 500 in the drawing, it is not limited thereto, and it may be formed on only one of the lower part and the upper part of the liquid crystal panel 500.

The optical film 100 includes the integrated polarization film 110 and the integrated compensation film 120, which are the same as described above.

Hereinafter, the present disclosure is illustrated in more detail with reference to examples. However, these examples are illustrative only, and the present disclosure is not limited thereto.

Synthesis of Monomer

Synthesis Example 1: Synthesis of Compound 1

Synthesis of Intermediate I-1

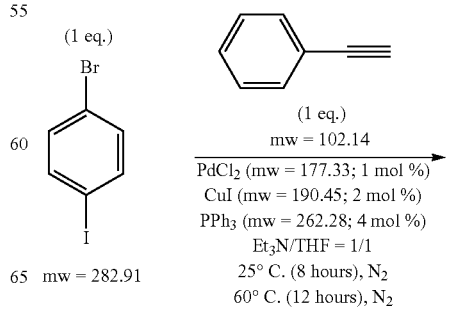

Reaction Scheme 1

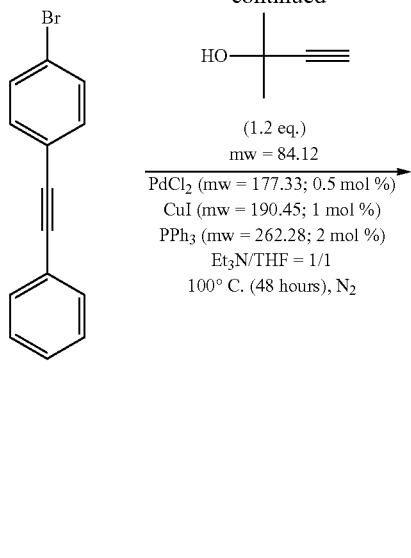

1-bromo-4-iodobenzene (mw=282.91 grams per mole (g/mol), v=0.5 moles (mol), m=141.46 grams (gr)) is dissolved in 1.5 liters (L) of a mixed solvent of triethylamine and tetrahydrofuran (volume to volume (v/v) of 1:1) in a 2 L round-bottomed flask to prepare a solution. Subsequently, the solution is purged with dry nitrogen gas for 1 hour (h). Subsequently, phenylacetylene (mw=102.14 g/mol, v=0.5 mol, m=51.1 gr), palladium(II) chloride (PdCl$_2$, mw=177.33 g/mol, v=0.005 mol, m=0.89 gr), copper(I) iodide (CuI) (mw=190.45 g/mol, v=0.01 mol, m=1.9 gr), and triphenylphosphine (PPh$_3$, mw=262.45 g/mol, v=0.02 mol, m=5.25 gr) are sequentially added to the solution. Then, the mixture is stirred at 25° C. for 8 h and at 60° C. for 12 h under a nitrogen atmosphere. Subsequently, 2-methyl-3-butyn-2-ol (mw=84.12 g/mol, v=0.6 mol, m=50.5 gr), palladium(II) chloride (PdCl$_2$, mw=177.33 mol, v=0.0025 mol, m=0.45 gr), copper(I) iodide (CuI) (mw=190.45 g/mol, v=0.005 mol, m=0.95 gr), and triphenylphosphine (PPh$_3$, mw=262.45 g/mol, v=0.01 mol, m=2.63 gr) are sequentially added thereto, and the mixture is stirred at 100° C. for 48 h under a nitrogen atmosphere. When the reaction is complete, the suspension is filtered to obtain a precipitate, and the precipitate is washed several times with a small amount of hot ethyl acetate. Then, the solvent is removed from the mother liquor under a reduced pressure, and the remaining solid is crystallized from ethyl acetate. The mother liquid is concentrated after the crystallization and dried at 60° C. under vacuum to obtain an intermediate I-1. The yield of the intermediate 1-1 is 88.3%.

Synthesis of Intermediate I-2

Intermediate I-1 (mw=260.34 mol, v=0.1 mol, m=26.3 gr) is dissolved in 0.5 L of toluene in a 1 L round-bottomed flask, and 32 milliliters (ml) of Bu$_4$NOH (10 percent by weight (wt %) in MeOH, 0.1 equivalents (eq.); d=0.82 grams per cubic centimeter (g/cm$^3$)) is added thereto. When the reaction is complete, the mixture is neutralized with acetic acid, and the solvent is removed therefrom under a reduced pressure. The obtained yellow solid is washed with water and dried at 60° C. under vacuum to obtain a yellow solid intermediate I-2. The yield of the intermediate I-2 is 95%.

Synthesis of Intermediate I-3

Reaction Scheme 3

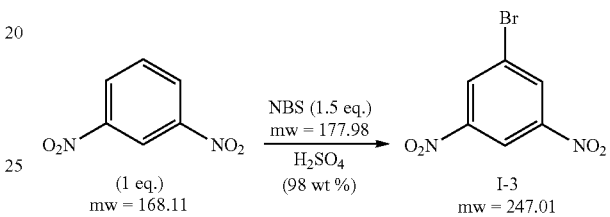

1,3-dinitrobenzene (mw=168.11 g/mol, v=0.6 mol, m=100.9 gr) is stirred and dissolved in 220 ml of H$_2$SO$_4$ (98 wt %) in a 1 L round-bottomed flask at 80° C. Subsequently, N-bromosuccinimide (mw=177.98 g/mol, v=0.9 mol, m=160.18 gr) is divided into 3 portions and separately added thereto. First, 0.6 mol of the N-bromosuccinimide is added to the solution, and the obtained mixture is stirred for 24 h, secondly, 0.18 mol of the N-bromosuccinimide is added thereto, and the obtained mixture is stirred for 24 h, and thirdly, 0.12 mol of the N-bromosuccinimide is added thereto, and the obtained mixture is stirred for 72 h. When the reaction is complete, the mixture is poured into 1 kilogram (kg) of ice to form a yellow solid. Subsequently, the yellow solid is filtered and washed with water. The obtained product is consecutively crystallized four times from a small amount of iso-propanol to obtain a green crystalline solid of an intermediate I-3. The yield of the intermediate I-3 is 52.1%.

Reaction Scheme 2

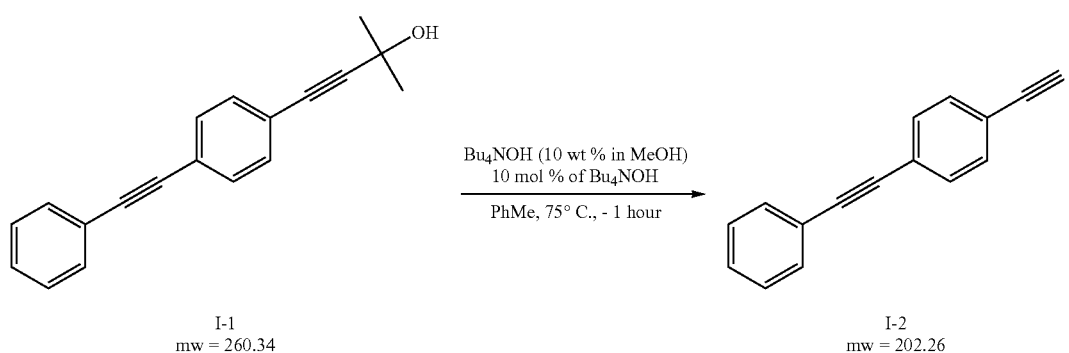

Synthesis of Intermediate I-4

Reaction Scheme 4

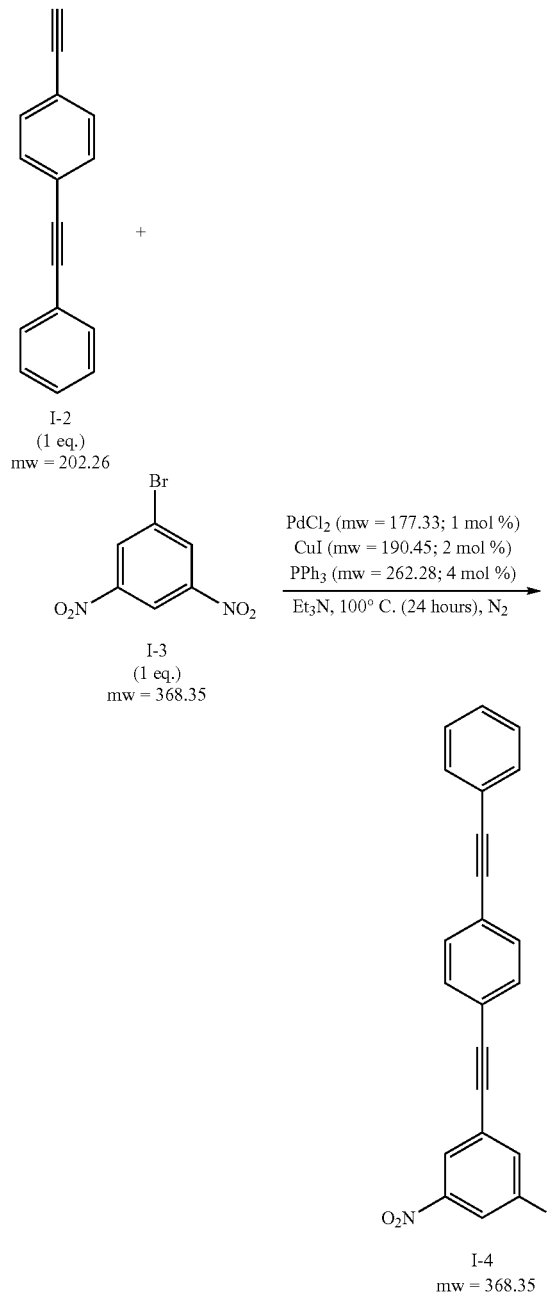

gr), and triphenylphosphine (PPh$_3$, mw=262.45 g/mol, v=0.00492 mol, m=1.29 gr) are sequentially added to the solution, and the mixture is refluxed at 100° C. for 24 h under a nitrogen atmosphere. When the reaction is complete, triethylamine is removed therefrom under reduced pressure, and the remaining solid is washed with water. The obtained product is suspended in hot iso-propanol and then filtered while cooled, which is repeated twice. The resulting product is dried at 80° C. under vacuum to obtain a light yellow crystalline solid of an intermediate I-4. The yield of the intermediate I-4 is 98.2%.

Synthesis of Final Compound (Compound 1)

Reaction Scheme 5

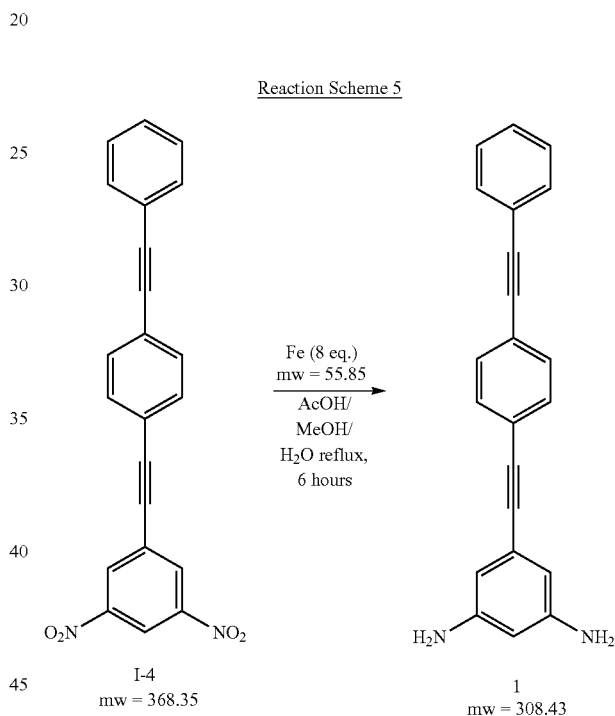

Intermediate I-2 (mw=202.26 g/mol, v=0.123 mol, m=24.88 gr) and the intermediate I-3 (mw=247.01 g/mol, v=0.123 mol, m=30.38 gr) are dissolved in 600 ml of triethylamine in a 1 L round-bottomed flask to prepare a solution. Subsequently, the solution is purged with dry nitrogen gas for 1 h. Then, palladium(II) chloride (PdCl$_2$, mw=177.33 g/mol, v=0.00123 mol, m=0.22 gr), copper(I) iodide (CuI) (mw=190.45 g/mol, v=0.00246 mol, m=0.47

Intermediate I-4 (mw=368.35 g/mol, v=0.119 mol, m=44 gr) is suspended in a boiling mixed solvent of 180 ml of acetic acid and 3 L of methanol in a 5 L flask. Subsequently, iron powder (mw=55.85 g/mol, v=0.952 mol, m=53.2 gr) is added to the suspension, and 100 ml of water is added thereto. Then, the mixture is refluxed for 6 h, and 200 ml of water is further added thereto. When the reaction is complete, 1 L of water is further added thereto, and the solid obtained by cooling down the obtained mixture is collected by filtration. Subsequently, the obtained solid is suspended in 300 ml of boiling methanol and then filtered while being cooled, which is repeated three times. The obtained product is dissolved in 300 ml of dimethyl acetamide and filtered, and then reprecipitated in 2 L of water. Subsequently, the precipitate is filtered and then suspended in iso-propanol to remove water therefrom. The obtained product is collected by filtration, and the obtained solid is suspended in 600 ml of boiling methanol and then filtered while being cooled. Then, the product obtained therefrom is dried at 70° C. under vacuum to obtain compound 1. The yield of the compound 1 is 67.1%.

$^1$H NMR (DMSO-d6) 300 MHz, δ, ppm: 4.92 (s, 4H, NH$_2$), 5.88 (dd, 1H, J$^{13}$=1.8 Hz), 6.00 (d, 2H, J$^{13}$=1.8 Hz), 7.45-7.58 (m, 9H).

Synthesis Example 2: Synthesis of Compound 2

Synthesis of Intermediate I-5

3.5-dinitrobenzoic acid (mw=212.12 g/mol, v=0.2 mol, m=42.42 gr), phosphorus pentachloride (PCl$_5$, mw=208.24 g/mol, v=0.2 mol, m=41.65 gr) and one drop of pyridine are added to 300 ml of toluene, and the mixture is stirred and refluxed for 12 h. Subsequently, toluene and POCl$_3$ are removed under reduced pressure, and the remaining residue is dissolved in 1 L of dichloromethane. Subsequently, 1-[2-(4-hydroxyphenyl)ethynyl]-4-(2-phenyl ethynyl)benzene (mw=194.24 g/mol, v=0.2 mol, m=58.8 gr) and triethylamine (Et$_3$N) (mw=101.24 g/mol, v=0.25 mol, m=48.56 gr) are sequentially added thereto, while the solution is stirred. Then, the mixture is refluxed for 30 min, and dichloromethane is removed therefrom under reduced pressure. The obtained brown solid is crystallized from a dichloromethane-ethanol mixed solvent to obtain an intermediate I-5. The yield of the intermediate I-5 is 93%.

Reaction Scheme 6

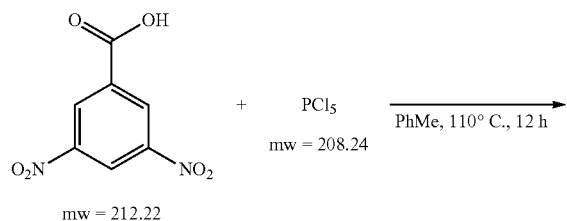

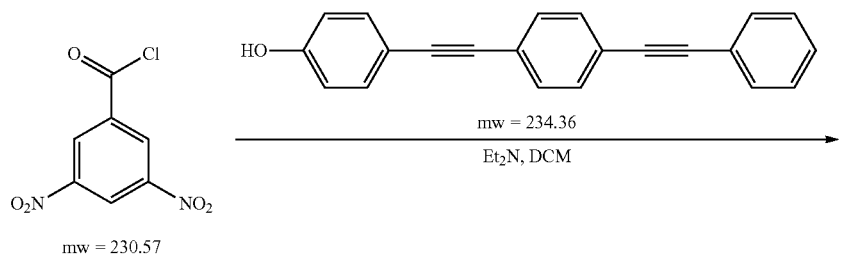

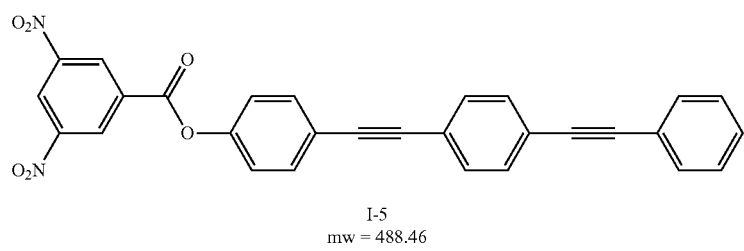

I-5
mw = 488.46

Synthesis of Final Compound (Compound 2)

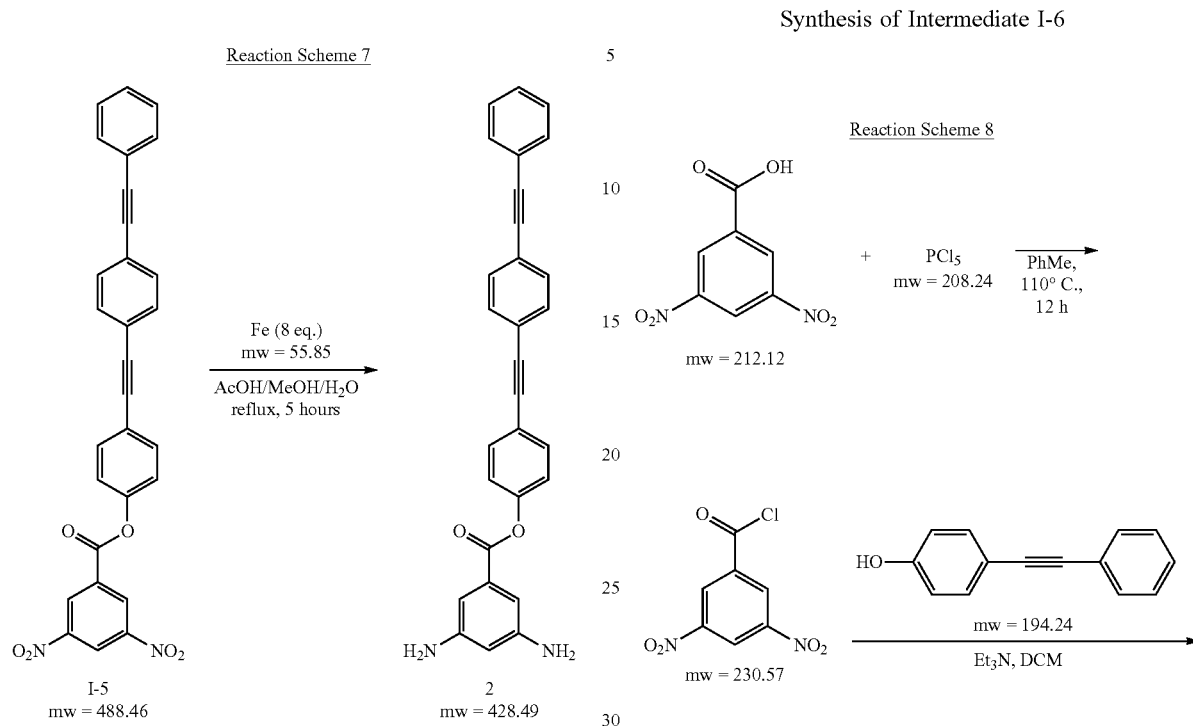

Intermediate I-5 (mw=488.46 g/mol, v=0.1 mol, m=48.5 gr) is suspended in a boiling mixed solvent of 180 ml of acetic acid and 3 L of methanol in a 5 L flask. Subsequently, a small amount of iron powder (mw=55.85 g/mol, v=0.8 mol, m=44.68 gr) is added to the suspension, and 100 ml of water is added thereto. Then, the mixture is refluxed for 5 h, and 500 ml of the water is further added thereto. When the reaction is complete, 1 L of water is further added thereto, the mixture is cooled to obtain a solid, and the solid is collect by filtration. Subsequently, the obtained solid is suspended in 400 ml of boiling iso-propanol and then filtered while being cooled, which is repeated three times. The obtained product is dissolved in 300 ml of dimethyl acetamide and filtered, and then reprecipitated in 2 L of water. The obtained precipitate is collected by filtration and then suspended in iso-propanol to remove water. Subsequently, the obtained product is collected by filtration, and the obtained solid is suspended in 600 ml of boiling methanol and then filtered while being cooled. The obtained product is dried at 70° C. under vacuum to obtain compound 2. The yield of compound 2 is 65.4%.

$^1$H NMR (DMSO-$d_6$) 300 MHz, δ, ppm: 4.92 (br. s, 4H, NH$_2$), 5.88 (dd, 1H, $J^{13}$=1.8 Hz), 6.00 (d, 2H, $J^{13}$=1.8 Hz), 7.42-7.60 (m, 13H).

Synthesis Example 3: Synthesis of Compound 3

Synthesis of Intermediate I-6

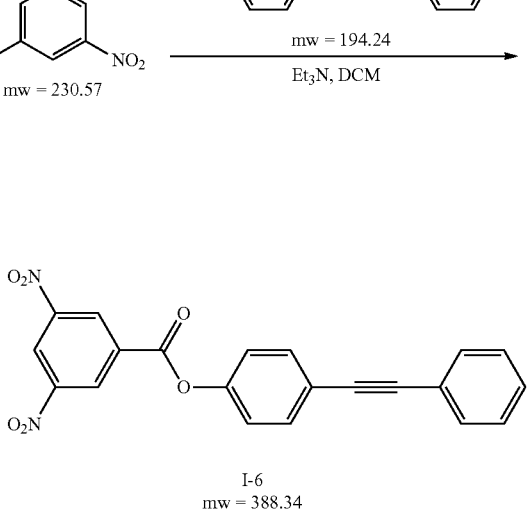

3.5-dinitrobenzoic acid (mw=212.12 g/mol, v=0.2 mol, m=42.42 gr), phosphorus pentachloride (PCl$_5$, mw=208.24 g/mol, v=0.2 mol, m=41.65 gr), and one drop of pyridine are added to 300 ml of toluene, and the mixture is stirred and refluxed for 12 h. Subsequently, the toluene and POCl$_3$ are removed under reduced pressure, and the remaining residue is dissolved in 1 L of dichloromethane. Subsequently, 4-hydroxydiphenylacetylene (mw=194.24 g/mol, v=0.2 mol, m=38.85 gr), and triethylamine (Et$_3$N) (mw=101.24 g/mol, v=0.25 mol, m=48.56 gr) are sequentially added thereto while the solution is stirred. Then, the mixture is refluxed for 30 min, and dichloromethane is removed therefrom under reduced pressure. The obtained brown solid is crystallized from a dichloromethane-ethanol mixed solvent to obtain an intermediate I-6. The yield of the intermediate I-6 is 95%.

Synthesis of Final Compound (Compound 3)

Reaction Scheme 9

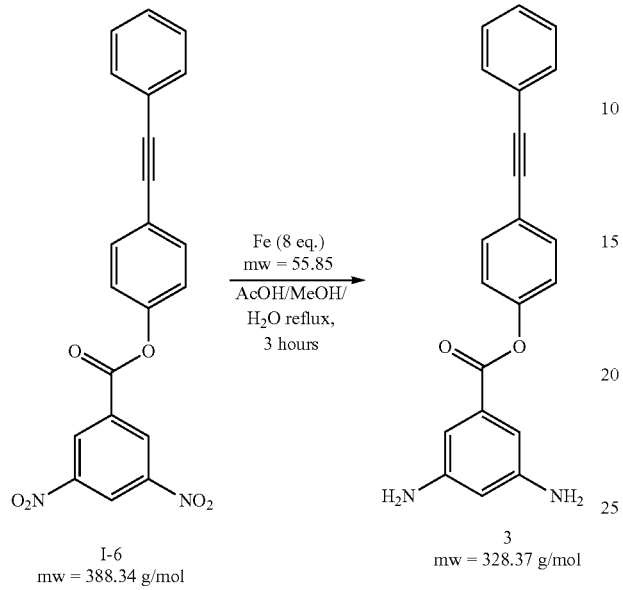

Intermediate I-6 (mw=388.34 g/mol, v=0.1 mol, m=38.8 gr) is suspended in a boiling mixed solvent of 180 ml of acetic acid and 2 L of methanol in a 5 L flask. Subsequently, a small amount of iron powder (mw=55.85 g/mol, v=0.8 mol, m=44.68 gr) is added to the suspend solution, and 100 ml of water is added thereto. Then, the mixture is refluxed for 3 h, and 500 ml of water is further added thereto. When the reaction is complete, 1 L of water is further added thereto, and the mixture is cooled and then extracted three times with 600 ml of ethyl acetate. The extracted solution is washed with water, dried with $Na_2SO_4$ and then concentrated under reduced pressure to obtain a white solid. The white solid precipitate is collected by filtration and washed with a small amount of cold ethyl acetate to obtain compound 3. The yield of the compound 3 is 60%.

$^1$H NMR (DMSO-$d_6$) 300 MHz, δ, ppm: 4.92 (br. s, 4H, $NH_2$), 5.88 (dd, 1H, $J^{13}$=1.8 Hz), 6.00 (d, 2H, $J^{13}$=1.8 Hz), 7.44-7.59 (m, 13H).

Synthesis Example 4: Synthesis of Compound 4

Synthesis of Intermediate I-7

Reaction Scheme 10

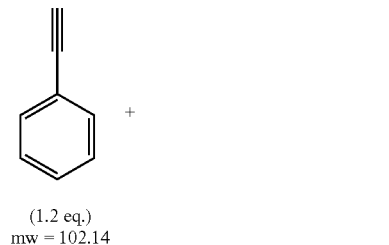

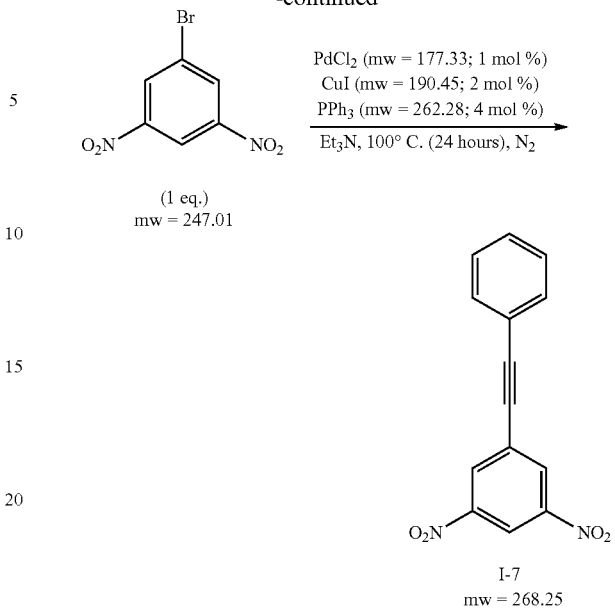

Phenylacetylene (mw=102.14 g/mol, v=0.197 mol, m=20.1 gr) and 3,5-dinitrobromobenzene (mw=247.01 g/mol, v=0.164 mol, m=40.5 gr) are dissolved in a mixed solvent of 300 ml of triethylamine and 100 ml of THF in a 1 L round-bottomed flask to prepare a solution. The solution is purged with dry nitrogen gas for 1 h. Subsequently, palladium(II) chloride ($PdCl_2$, mw=177.33 g/mol, v=0.00164 mol, m=0.29 gr), copper(I) iodide (CuI) (mw=190.45 g/mol, v=0.00328 mol, m=0.62 gr), and triphenylphosphine ($PPh_3$, mw=262.45 g/mol, v=0.00656 mol, m=1.72 gr) are sequentially added to the solution, and the mixture is refluxed at 100° C. for 24 h under a nitrogen atmosphere. When the reaction is complete, triethylamine is removed under reduced pressure, and the remaining solid is washed. The obtained product is suspended in boiling ethyl acetate and then filtered while being cooled, which is repeated twice. Then, the product obtained therefrom is dried at 80° C. under vacuum to obtain a yellow crystalline solid of an intermediate I-7. The yield of the intermediate I-7 is 75%.

Synthesis of Final Compound (Compound 4)

Reaction Scheme 11

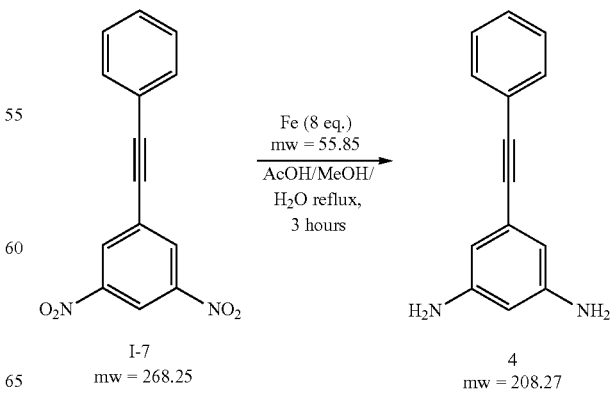

Intermediate I-7 (mw=268.25 g/mol, v=0.112 mol, m=30 gr) is suspended in a boiling mixed solvent of 180 ml of acetic acid and 2 L of methanol in a 5 L flask. Subsequently, iron powder (mw=55.85 g/mol, v=0.896 mol, m=50 gr) is added to the suspension, and 100 ml of water is added thereto. The mixture is refluxed for 3 h, and 500 ml of water is further added thereto. When the reaction is complete, 1 L of water is added thereto, and the mixture is cooled and then extracted three times with 600 ml of ethyl acetate. The extracted solution is washed with water, and solvent is removed therefrom under reduced pressure. Then, 2 equivalents of concentrated hydrochloric acid are added to the product obtained therefrom to obtain a precipitate. The precipitate is suspended in boiling acetone and then collected by filtration. The obtained solid is dissolved in 1 L of hot water and treated with charcoal, and then filtered. Subsequently, an ammonium hydroxide aqueous solution is added thereto to obtain a white precipitate. The precipitate is filtered and washed with water and then dried at 70° C. for 24 h under a reduced pressure to obtain compound 4.

$^1$H NMR (DMSO-d6) 300 MHz, δ, ppm: 4.90 (br. s, 4H, NH$_2$), 5.87 (dd, 1H, J$^{13}$=1.8 Hz), 5.99 (d, 2H, J$^{13}$=1.8 Hz), 7.37-7.50 (m, 5H).

Synthesis of Polymer

Synthesis Example 5

Compound 1 according to Synthesis Example 1 and the compound 5 represented by Chemical Formula A-1 (2,2'-bis(trifluoromethyl)-4,4'-diaminobiphenyl, Tokyo Chemical Industry) in a mole ratio of 5:5 are dissolved in dimethyl acetamide to prepare a solution. The compound 6 represented by Chemical Formula B-1 (4,4'-oxydiphthalic anhydride, Tokyo Chemical Industry) is added thereto, and the mixture is reacted at room temperature for 48 h to prepare a composition. The composition includes compound 1, compound 5, and compound 6 in a mole ratio of 5:5:10. When the reaction is complete, the composition is spin coated on a 5×5 square centimeters (cm$^2$) glass plate at 1,000 revolutions per minute (rpm) for 1 minute (min) and dried in an 80° C. oven for 2 h to form a 15 micrometer (μm)-thick polymer film.

The polymer has a structural unit of Chemical Formula C-1 and a weight average molecular weight of 260,000 g/mol.

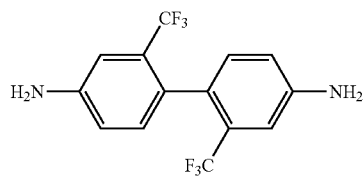

Chemical Formula A-1

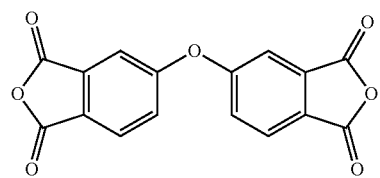

Chemical Formula B-1

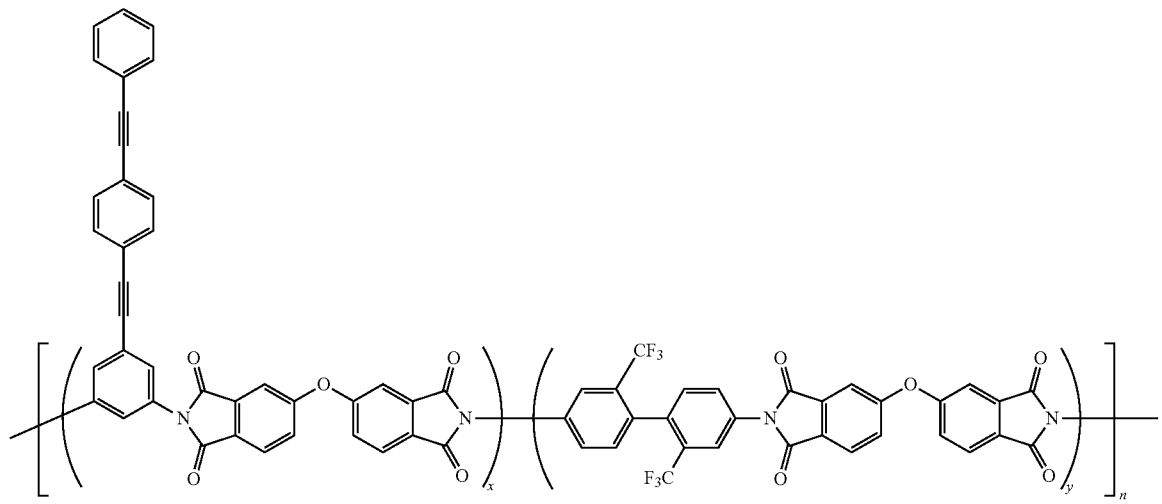

Chemical Formula C-1

(x:y = 5:5)

Synthesis Example 6

A polymer film is formed according to the same method as Synthesis Example 5, except for including compound 1, compound 5, and compound 6 in a mole ratio of 1:9:10. The polymer has a structural unit of Chemical Formula C-2 and a weight average molecular weight of 280,000 g/mol.

Chemical Formula C-2

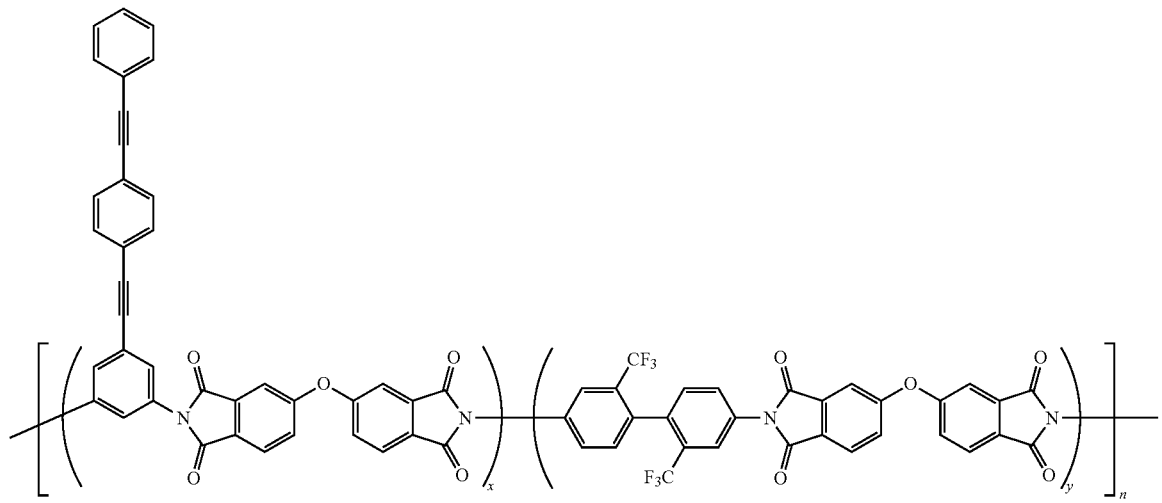

(x:y = 1:9)

Synthesis Example 7

A polymer film is prepared according to the same method as Synthesis Example 5, except for including compound 1, compound 5, and compound 6 in a mole ratio of 2:8:10. The polymer has a structural unit of Chemical Formula C-3 and a weight average molecular weight of 270,000 g/mol.

Chemical Formula C-3

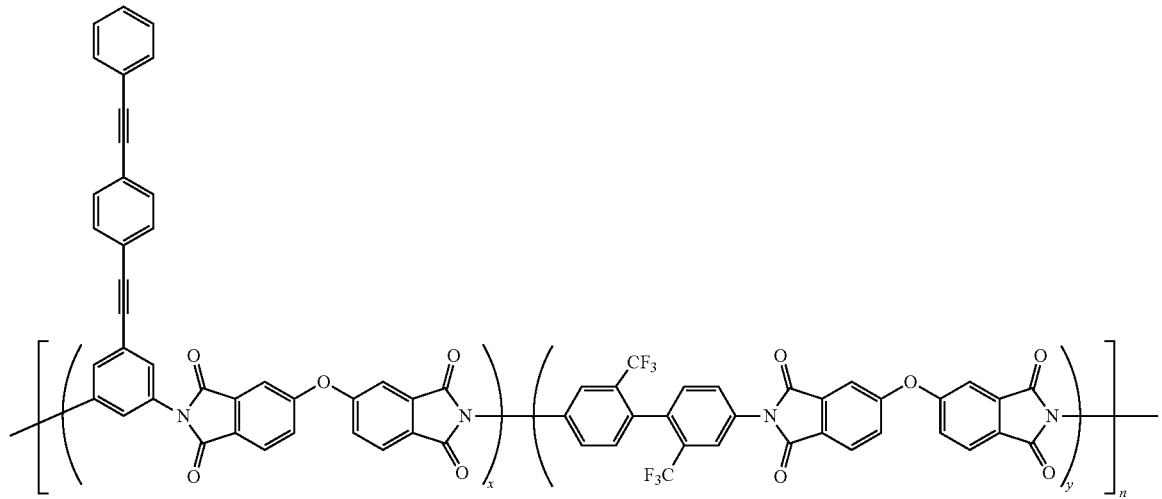

(x:y = 2:8)

Synthesis Example 8

A polymer film is prepared according to the same method as Synthesis Example 5, except for including compound 1, compound 5, and compound 6 in a mole ratio of 3:7:10. The polymer has a structural unit of Chemical Formula C-4 and a weight average molecular weight of 250,000 g/mol.

Synthesis Example 10

Compound 3 according to Synthesis Example 3 and compound 7 represented by Chemical Formula A-2 (4,4'-oxydianiline, Sigma-Aldrich Co. Ltd.) in a mole ratio of 1:9 are dissolved in dimethyl acetamide to prepare a solution. Compound 8 represented by Chemical Formula B-2 (ben- Chemical Formula C-4

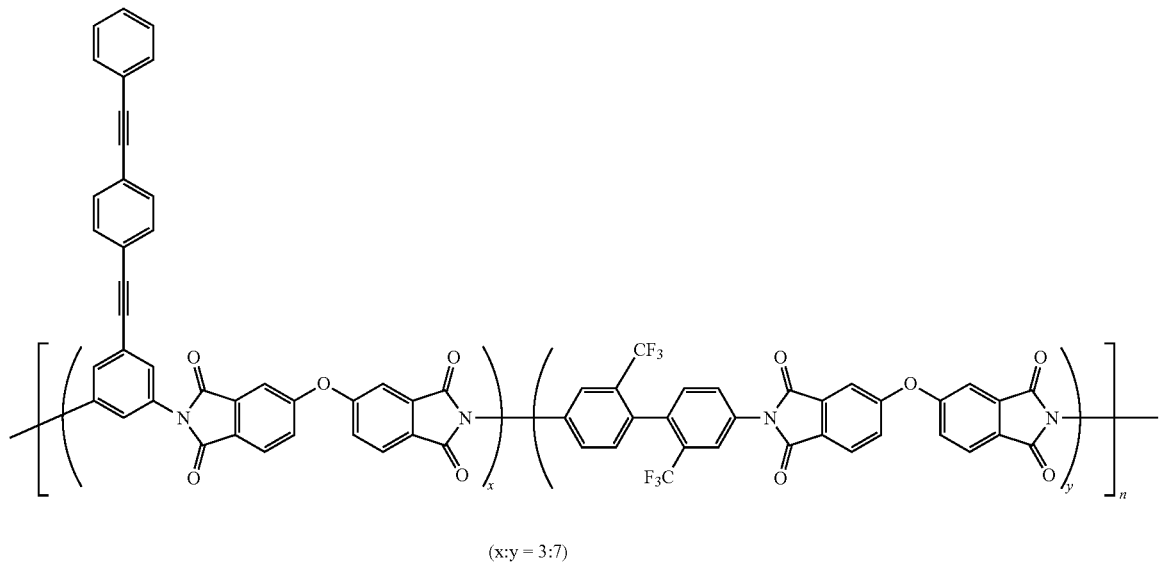

(x:y = 3:7)

Synthesis Example 9

A polymer film is prepared according to the same method as Synthesis Example 5, except for including compound 1, compound 5, and compound 6 in a mole ratio of 4:7:10. The polymer has a structural unit of Chemical Formula C-5 and a weight average molecular weight of 270,000 g/mol.

zene-1,2,4,5-tetracarboxylic dianhydride, Sigma-Aldrich Co., Ltd.) is added thereto, and the mixture is reacted at room temperature for 48 h under a nitrogen atmosphere to prepare a composition. The composition includes compound 3, compound 7, and compound 8 in a mole ratio of 1:9:10. When the reaction is complete, the composition is spin Chemical Formula C-5

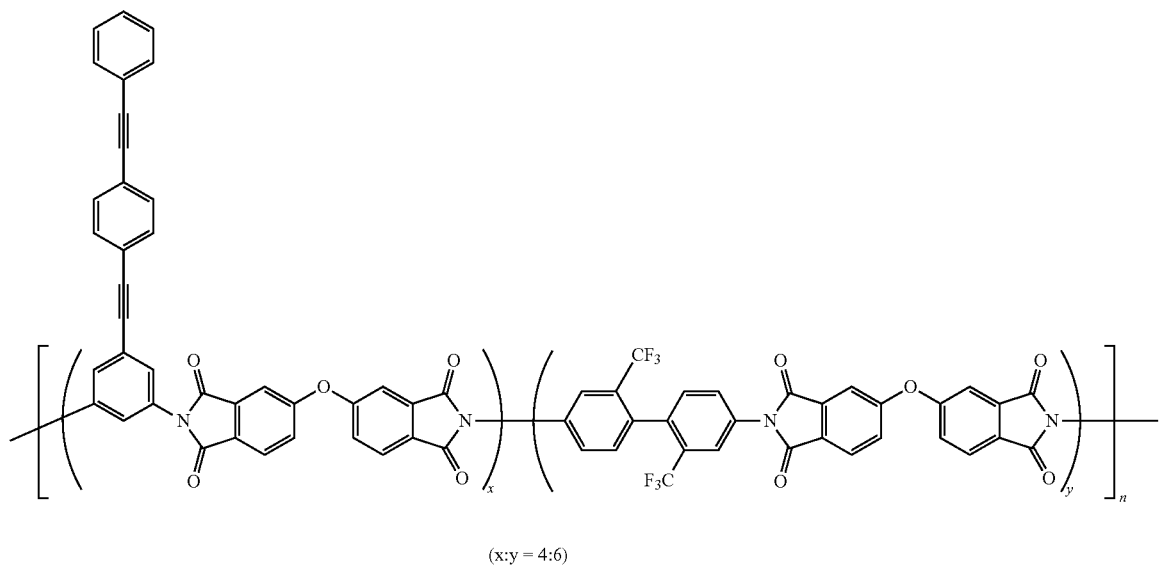

(x:y = 4:6)

coated on a 5×5 cm² glass plate at 1,000 rpm for 1 min and dried in an 80° C. oven for 2 h to form a 15 μm-thick polymer film.

The polymer has a structural unit of Chemical Formula D-1 and a weight average molecular weight of 240,000 g/mol.

Synthesis Example 11

A polymer film is prepared according to the same method as Synthesis Example 10, except for including compound 3, compound 7, and compound 8 in a mole ratio of 2:8:10. The polymer has a structural unit of Chemical Formula D-2 and a weight average molecular weight of 260,000 g/mol.

Chemical Formula A-2

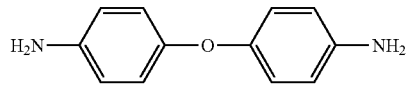

Chemical Formula B-2

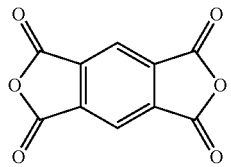

Chemical Formula D-1

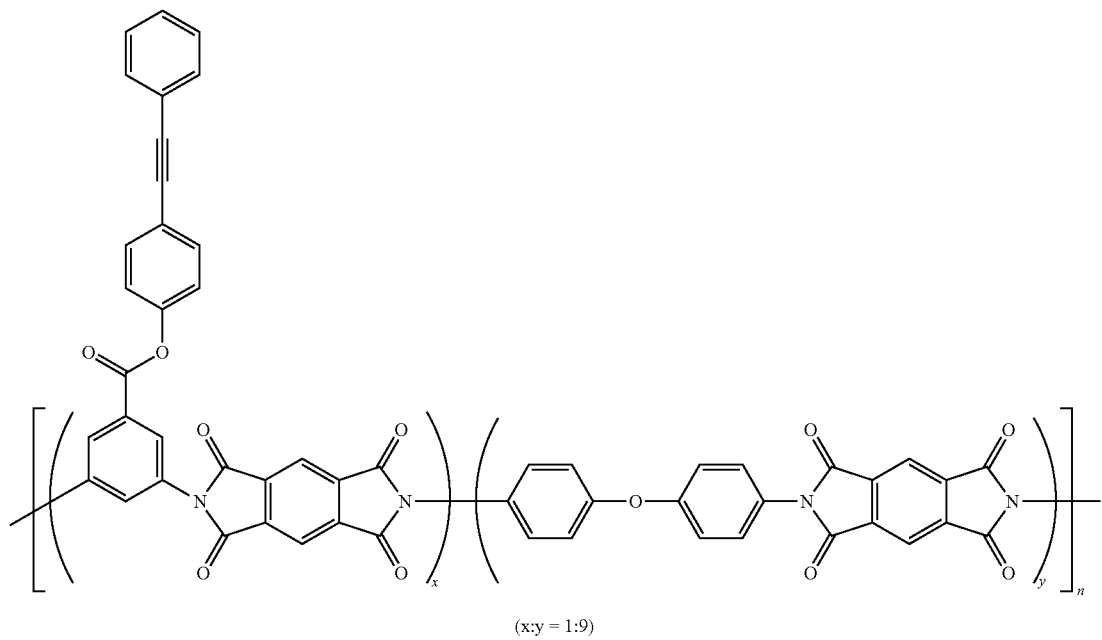

(x:y = 1:9)

Chemical Formula D-2

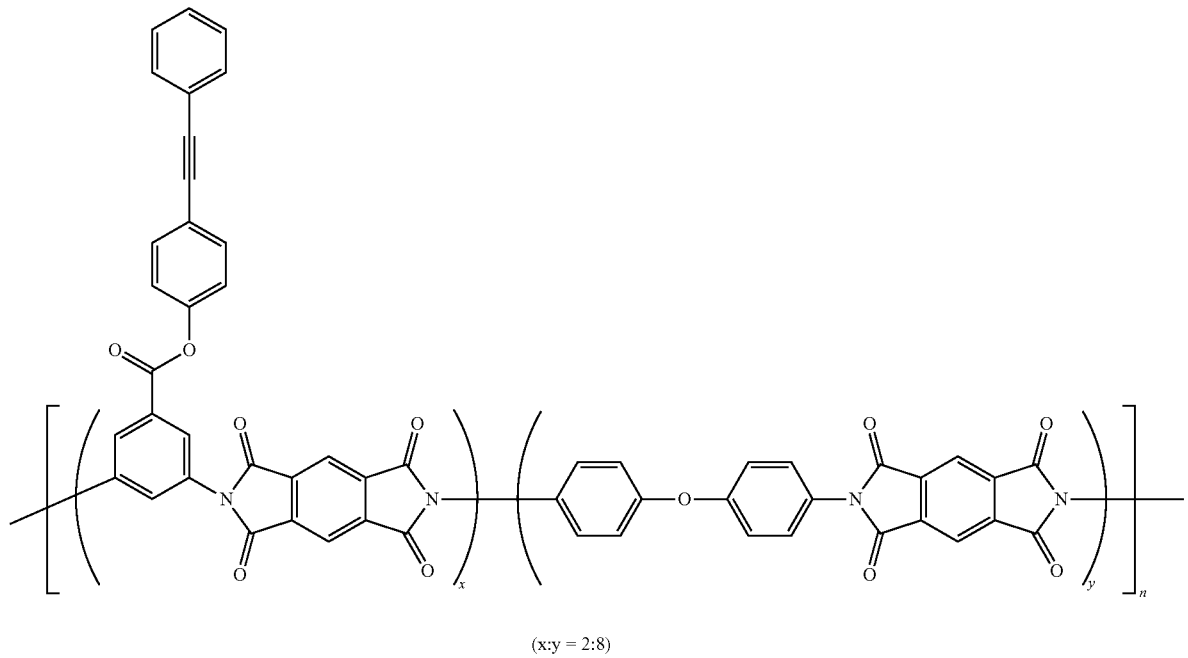

(x:y = 2:8)

Compensation Film

Example 1

The polymer film according to Synthesis Example 5 is detached from the glass plate and cut to a size of 15×45 square millimeters (mm$^2$) to obtain a sample, and an elongated compensation film having an average thickness of about 12 μm is prepared by fixing the long side of the sample at a metal frame, putting it in an oven under a nitrogen atmosphere, and heating it up to 300° C. at 10 degree Centigrade per minute (° C./min) for 1 h.

Example 2

An elongated compensation film is prepared according to the same method as Example 1, except for using the polymer film according to Synthesis Example 6 instead of the polymer film according to Synthesis Example 5.

Example 3

An elongated compensation film is prepared according to the same method as Example 1, except for using the polymer film according to Synthesis Example 7 instead of the polymer film according to Synthesis Example 5.

Example 4

An elongated compensation film is prepared according to the same method as Example 1, except for using the polymer film according to Synthesis Example 8 instead of the polymer film according to Synthesis Example 5.

Example 5

An elongated compensation film is prepared according to the same method as Example 1, except for using the polymer film according to Synthesis Example 9 instead of the polymer film according to Synthesis Example 5.

Example 6

An elongated compensation film is prepared according to the same method as Example 1, except for using the polymer film according to Synthesis Example 10 instead of the polymer film according to Synthesis Example 5.

Example 7

An elongated compensation film is prepared according to the same method as Example 1, except for using the polymer film according to Synthesis Example 11 instead of the polymer film according to Synthesis Example 5.

Evaluation

Evaluation 1

The retardation values of the compensation films according to Examples 1 to 7 are measured.

The retardation value is measured by using Axoscan equipment (Axometrics Inc.). The reference wavelength of the retardation is about 550 nanometers (nm).

The results are provided in Table 1.

TABLE 1

|  | In-plane retardation ($R_o$, nm) | Thickness direction retardation ($R_{th}$, nm) |
| --- | --- | --- |
| Example 1 | 138 | 65 |
| Example 2 | 137 | 65 |
| Example 3 | 138 | 66 |
| Example 4 | 142 | 68 |
| Example 5 | 139 | 67 |

TABLE 1-continued

| | In-plane retardation ($R_o$, nm) | Thickness direction retardation ($R_{th}$, nm) |
|---|---|---|
| Example 6 | 137 | 64 |
| Example 7 | 135 | 63 |

Referring to Table 1, the compensation films according to Examples 1 to 7 have in-plane retardation values ranging from about 110 to 160 nm and may be used as a λ/4 phase delay layer.

Evaluation 2

The wavelength dispersion values of the compensation films according to Examples 1 to 7 are evaluated.
The wavelength dispersion value is measured by using Axoscan equipment (Axometrics Inc.).
The results are provided in Table 2.

TABLE 2

| | R (450 nm)/R (550 nm) | R (650 nm)/R (550 nm) |
|---|---|---|
| Example 1 | 0.84 | 1.06 |
| Example 2 | 1.07 | 0.96 |
| Example 3 | 1.04 | 0.96 |
| Example 4 | 1.01 | 0.95 |
| Example 5 | 1.00 | 0.98 |
| Example 6 | 1.05 | 0.98 |
| Example 7 | 0.95 | 0.98 |

Referring to Table 2, the compensation films according to Examples 1 to 7 show different retardation values depending on a wavelength, and specifically, the compensation films according to Examples 1 and 7 have a reverse wavelength dispersion phase delay of which retardation regarding light at a long wavelength is larger than retardation regarding light at a short wavelength, and the compensation films according to Examples 2 to 6 show a normal wavelength dispersion phase delay of which retardation regarding light at a long wavelength is smaller than retardation regarding light at a short wavelength.

While this disclosure has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims.

What is claimed is:

1. A polymer, which is a reaction product of an anhydride and a diamine compound, wherein the diamine compound comprises a first diamine compound represented by Chemical Formula 1-1:

Chemical Formula 1-1

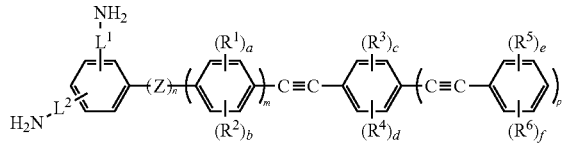

wherein, in Chemical Formula 1-1,

Z is —C=O—, —(C=O)O—, —O(C=O)—, —CH$_2$O—, —CF$_2$O—, —OC(=O)O—, —C≡C—, —CH=CH—, —CF=CF—, or —C(=O)NR$^a$—,

L$^1$ and L$^2$ are independently a single bond, a substituted or unsubstituted C1 to C20 alkylene group, a substituted or unsubstituted C1 to C20 oxyalkylene group, a substituted or unsubstituted C3 to C20 cycloalkylene group, a substituted or unsubstituted C3 to C20 oxycycloalkylene group, a substituted or unsubstituted C6 to C20 arylene group, a substituted or unsubstituted C6 to C20 oxyarylene group, a substituted or unsubstituted C3 to C20 divalent heterocyclic group, or a combination thereof, R$^1$ to R$^6$ and R$^a$ are independently hydrogen, a substituted or unsubstituted C1 to C20 alkyl group, a substituted or unsubstituted C1 to C20 alkoxy group, a substituted or unsubstituted C2 to C20 alkoxyalkyl group, a substituted or unsubstituted C1 to C20 fluoroalkyl group, a substituted or unsubstituted C3 to C20 cycloalkyl group, a substituted or unsubstituted C3 to C20 cycloalkyloxy group, a substituted or unsubstituted C4 to C20 cycloalkoxyalkyl group, a substituted or unsubstituted C6 to C20 aryl group, a substituted or unsubstituted C6 to C20 aryloxy group, a substituted or unsubstituted C7 to C20 arylalkyl group, a substituted or unsubstituted C7 to C20 aryloxyalkyl group, a substituted or unsubstituted C3 to C20 heterocyclic group, a substituted or unsubstituted silyl group, a hydroxy group, a halogen, a nitro group, or a combination thereof, n and m are independently 0 or 1,
p is an integer ranging from 1 to 3,
a to f are independently integers ranging from 0 to 4, and
a+b, c+d, and e+f are independently integers of less than or equal to 4.

2. The polymer of claim 1, wherein the first diamine compound is represented by Chemical Formula 1-1a or 1-1b:

Chemical Formula 1-1a

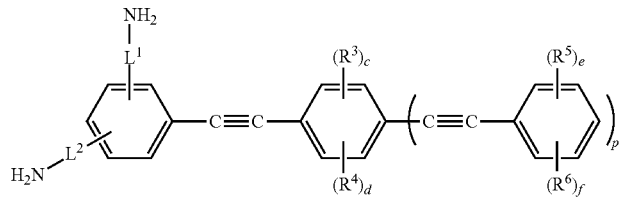

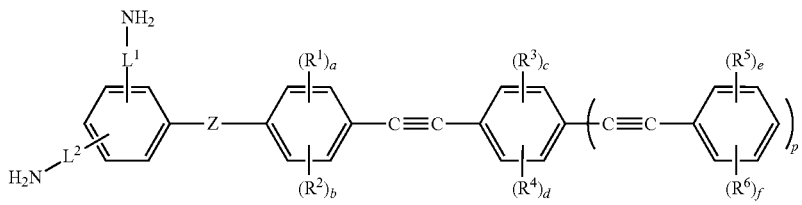

Chemical Formula 1-1b wherein, in Chemical Formulae 1-1a and 1-1b,
Z is —C=O—, —(C=O)O—, —O(C=O)—, —CH$_2$O—, —CF$_2$O—, —OC(=O)O—, —C≡C—, —CH=CH—, —CF=CF—, or —C(=O)NR$^a$—,
L$^1$ and L$^2$ are independently a single bond, a substituted or unsubstituted C1 to C20 alkylene group, a substituted or unsubstituted C1 to C20 oxyalkylene group, a substituted or unsubstituted C3 to C20 cycloalkylene group, a substituted or unsubstituted C3 to C20 oxycycloalkylene group, a substituted or unsubstituted C6 to C20 arylene group, a substituted or unsubstituted C6 to C20 oxyarylene group, a substituted or unsubstituted C3 to C20 divalent heterocyclic group, or a combination thereof,
R$^1$ to R$^6$ and R$^a$ are independently hydrogen, a substituted or unsubstituted C1 to C20 alkyl group, a substituted or unsubstituted C1 to C20 alkoxy group, a substituted or unsubstituted C2 to C20 alkoxyalkyl group, a substituted or unsubstituted C1 to C20 fluoroalkyl group, a substituted or unsubstituted C3 to C20 cycloalkyl group, a substituted or unsubstituted C3 to C20 cycloalkyloxy group, a substituted or unsubstituted C4 to C20 cycloalkoxyalkyl group, a substituted or unsubstituted C6 to C20 aryl group, a substituted or unsubstituted C6 to C20 aryloxy group, a substituted or unsubstituted C7 to C20 arylalkyl group, a substituted or unsubstituted C7 to C20 aryloxyalkyl group, a substituted or unsubstituted C3 to C20 heterocyclic group, a substituted or unsubstituted silyl group, a hydroxy group, a halogen, a nitro group, or a combination thereof, p is an integer ranging from 1 to 3,
a to f are independently integers ranging from 0 to 4, and a+b, c+d, and e+f are independently integers of less than or equal to 4.

3. The polymer of claim 1, wherein the first diamine compound is represented by Chemical Formula 1a or 1b:

4. The polymer of claim 1,
wherein the diamine compound further comprises a second diamine compound, which is different from the first diamine compound, and
wherein the second diamine compound comprises at least one selected from compounds of Group 1:

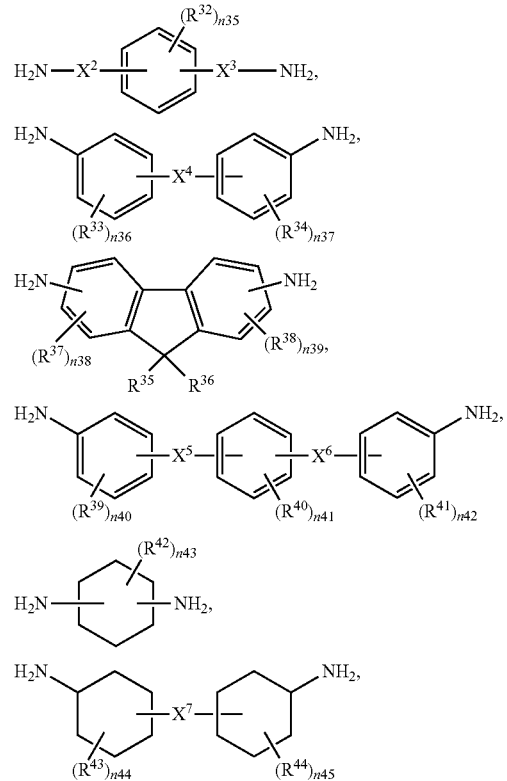

Group 1

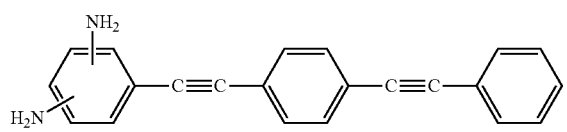

Chemical Formula 1a

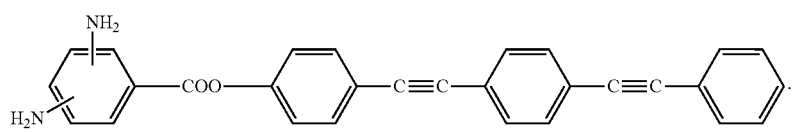

Chemical Formula 1b

-continued

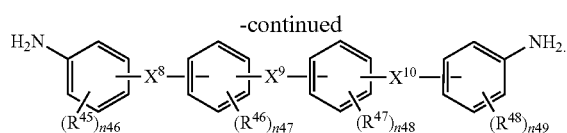

wherein, in Group 1, $R^{32}$ to $R^{48}$ are independently hydrogen, a substituted or unsubstituted C1 to C20 alkyl group, a substituted or unsubstituted C1 to C20 alkoxy group, a substituted or unsubstituted C1 to C20 fluoroalkyl group, a substituted or unsubstituted C3 to C20 cycloalkyl group, a substituted or unsubstituted C3 to C20 heterocyclic group, a substituted or unsubstituted C3 to C20 cycloalkoxy group, a substituted or unsubstituted C6 to C20 aryl group, a substituted or unsubstituted C6 to C20 aryloxy group, a substituted or unsubstituted amine group, a substituted or unsubstituted C1 to C20 alkylamine group, a substituted or unsubstituted silyl group, a hydroxy group, a halogen, a nitro group, or a combination thereof, $X^2$ to $X^{10}$ are independently a single bond, a substituted or unsubstituted C1 to C20 alkylene group, a substituted or unsubstituted C3 to C20 cycloalkylene group, a substituted or unsubstituted C6 to C20 arylene group, a substituted or unsubstituted C3 to C20 divalent heterocyclic group, —SO$_2$—, —O—, —C(═O)—, —C(═O)O—, a group selected from Group 2, or a combination thereof, n35 to n37 and n40 to n49 are independently an integer ranging from 0 to 4, and n38 and n39 are independently an integer ranging from 0 to 3, Group 2

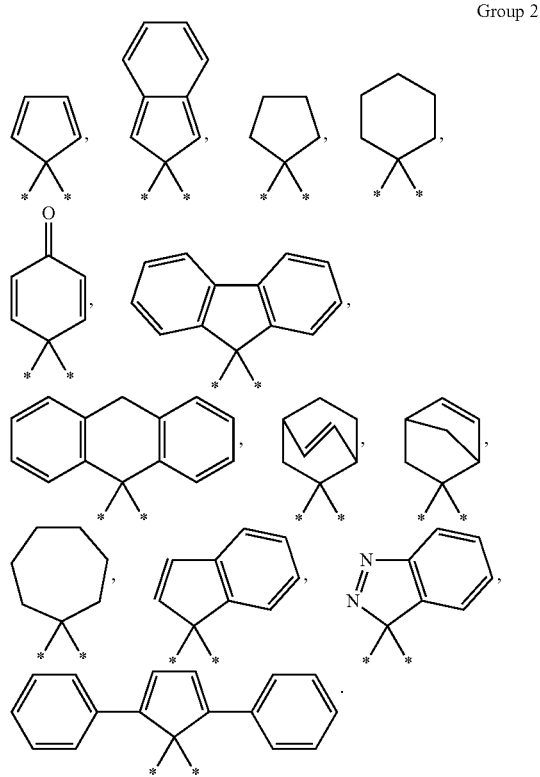

5. The polymer of claim 4, wherein the second diamine compound comprises at least one selected from compounds of Group 3:

Group 3

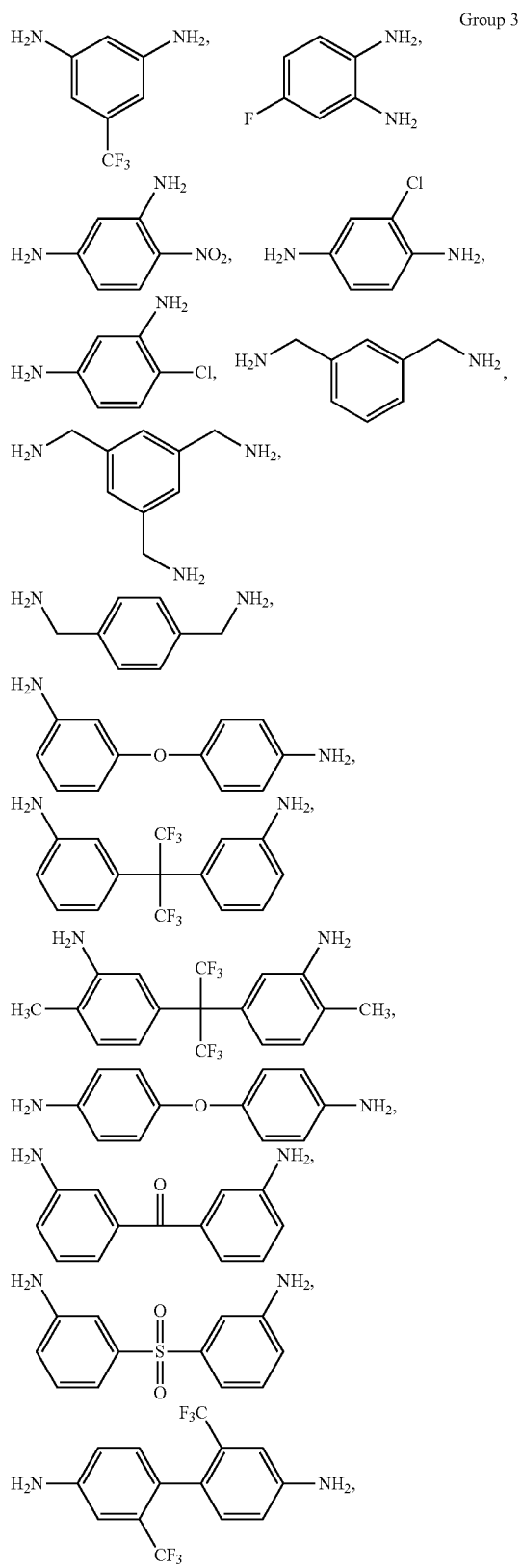

-continued

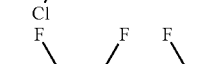
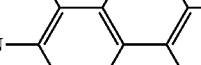
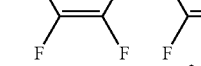
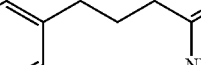
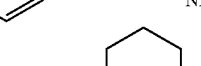
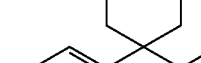
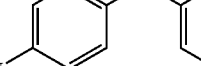
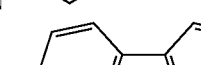
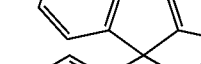
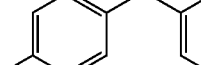

6. The polymer of claim 4, wherein a mole ratio of the first diamine compound and the second diamine compound is about 1:9 to about 5:5.

7. The polymer of claim 1, wherein the anhydride is represented by Chemical Formula 2 or 3:

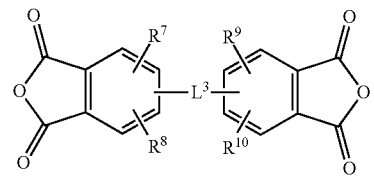

Chemical Formula 2

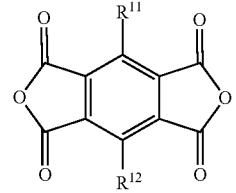

Chemical Formula 3 wherein, in Chemical Formula 2 or 3, $L^3$ is a single bond, a substituted or unsubstituted C1 to C20 alkylene group, a substituted or unsubstituted C1 to C20 oxyalkylene group, a substituted or unsubstituted C3 to C20 cycloalkylene group, a substituted or unsubstituted C3 to C20 oxycycloalkylene group, a substituted or unsubstituted C6 to C20 arylene group, a substituted or unsubstituted C6 to C20 oxyarylene group, a substituted or unsubstituted C3 to C20 divalent heterocyclic group, —O—, —C(=O)—, —C(=O)O—, —SO₂—, —C(=O)NR$^b$—, or a combination thereof, and $R^7$ to $R^{12}$ and $R^b$ are independently hydrogen, a substituted or unsubstituted C1 to C20 alkyl group, a substituted or unsubstituted C1 to C20 alkoxy group, a substituted or unsubstituted C2 to C20 alkoxyalkyl group, a substituted or unsubstituted C1 to C20 fluoroalkyl group, a substituted or unsubstituted C3 to C20 cycloalkyl group, a substituted or unsubstituted C3 to C20 cycloalkyloxy group, a substituted or unsubstituted C4 to C20 cycloalkoxyalkyl group, a substituted or unsubstituted C6 to C20 aryl group, a substituted or unsubstituted C6 to C20 aryloxy group, a substituted or unsubstituted C7 to C20 arylalkyl group, a substituted or unsubstituted C7 to C20 aryloxyalkyl group, a substituted or unsubstituted C3 to C20 heterocyclic group, a substituted or unsubstituted silyl group, a hydroxy group, a halogen, a nitro group, or a combination thereof.

8. The polymer of claim 1, wherein the anhydride comprises 2,3,3',4'-biphenyltetracarboxylic dianhydride, 2,3,3',4'-diphenylsulfone tetracarboxylic dianhydride, 3,4'-oxydiphthalic anhydride, 3,3',4,4'-biphenyl tetracarboxylic dianhydride, bicyclo[2.2.2]oct-7-ene-2,3,5,6-tetracarboxylic dianhydride, 3,3',4,4'-diphenylsulfone tetracarboxylic dianhydride, 4,4'-(hexafluoroisopropylidene)diphthalic anhydride, 4,4'-oxydiphthalic anhydride, pyromellitic dianhydride, 4-(2,5-dioxotetrahydrofuran-3-yl)-1,2,3,4-tetrahydronaphthalene-1,2-dicarboxylic anhydride, or a combination thereof.

* * * * *